(12) United States Patent
Suh et al.

(10) Patent No.: US 7,671,028 B2
(45) Date of Patent: Mar. 2, 2010

(54) PEPTIDES THAT ANTAGONIZE FPR CLASS RECEPTOR MEDIATED SIGNALING

(75) Inventors: Pann-Ghill Suh, Kyungsangbuk-do (KR); Yoe-Sik Bae, Busan (KR); Sung Ho Ryu, Kyungsangbuk-do (KR); Tae Hoon Lee, Kyungsangbuk-do (KR); Ha Young Lee, Busan (KR); Eun Jin Jo, Busan (KR); Jung-Im Kim, Busan (KR); Hyun-Kyu Kang, Ulsan (KR); Richard D. Ye, Westmont, IL (US); Jong-Young Kwak, Busan (KR)

(73) Assignees: POSTECH Foundation, Pohang (KR); POSCO, Pohang (KR); POSTECH Academy-Industry Foundation, Pohang (KR)

( * ) Notice: Subject to any disclaimer, the term of this patent is extended or adjusted under 35 U.S.C. 154(b) by 515 days.

(21) Appl. No.: 10/597,591

(22) PCT Filed: Feb. 3, 2005

(86) PCT No.: PCT/KR2005/000329
§ 371 (c)(1),
(2), (4) Date: Aug. 16, 2006

(87) PCT Pub. No.: WO2005/075505
PCT Pub. Date: Aug. 18, 2005

(65) Prior Publication Data
US 2008/0274978 A1    Nov. 6, 2008

Related U.S. Application Data

(60) Provisional application No. 60/541,730, filed on Feb. 4, 2004.

(51) Int. Cl.
*A61K 38/00* (2006.01)
*C07K 17/00* (2006.01)

(52) U.S. Cl. .............................. 514/17; 514/16; 514/15; 514/14; 514/825; 530/329; 530/328; 530/327

(58) Field of Classification Search .................. 514/17, 514/16, 15, 14, 825; 530/329, 328, 327
See application file for complete search history.

(56) References Cited

U.S. PATENT DOCUMENTS

| 5,324,716 A | * | 6/1994 | Selsted et al. ................. 514/14 |
| 2003/0096260 A1 | | 5/2003 | Miao et al. |
| 2003/0203841 A1 | | 10/2003 | Wang et al. |

FOREIGN PATENT DOCUMENTS

| WO | WO 2005/024057 | * | 3/2005 |
| WO | WO 2005/024058 | * | 3/2005 |

OTHER PUBLICATIONS

Bae et al., "Differential Activation of Formyl Peptide Receptor-Like 1 by Peptide Ligands," Journal of Immunology, 171:12 6807-6813 (2003).
Bae et al., "Differential Activation of Formyl Peptide Receptor Signlaing by Peptide Ligands," Molecular Pharmacology, 64:4 841-847 (2003).
Bae et al., "Identification of Peptides That Antagonize Formyl Peptide Receptor-Like 1-Mediated Signaling," Journal of Immunology, 173:1 607-614 (2004).

* cited by examiner

*Primary Examiner*—Jon P Weber
*Assistant Examiner*—Abdel A Mohamed
(74) *Attorney, Agent, or Firm*—Joseph H. Kim; JHK Law

(57) ABSTRACT

The present application discloses W-rich peptide that is useful for inhibiting FPR class receptor activity.

7 Claims, 8 Drawing Sheets
(1 of 8 Drawing Sheet(s) Filed in Color)

SEQUENCE LISTING

```
<160> NUMBER OF SEQ ID NOS: 36

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

Met Tyr Phe Ile Asn Ile Leu Thr Leu
 1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic

<400> SEQUENCE: 2
```

```
Trp Lys Tyr Met Val Met
 1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (6)
<223> OTHER INFORMATION: Xaa is m or D-Met while M is L-Met

<400> SEQUENCE: 3

Trp Lys Tyr Met Val Xaa
 1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

Trp Arg Trp Trp Trp Trp
 1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

Arg Arg Trp Trp Trp Trp
 1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

Arg His Trp Trp Trp Trp
 1               5

<210> SEQ ID NO 7
<211> LENGTH: 3
<212> TYPE: PRT
<213> ORGANISM: Artificial Sequence
<220> FEATURE:
<223> OTHER INFORMATION: Synthetic

<400> SEQUENCE: 7

Trp Arg Trp
 1

<210> SEQ ID NO 8
<211> LENGTH: 6
<212> TYPE: PRT
<213> ORGANISM: Artificial Sequence
<220> FEATURE:
<223> OTHER INFORMATION: Synthetic
```

```
<400> SEQUENCE: 8

Asp Arg Trp Trp Trp Trp
  1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic

<400> SEQUENCE: 9

Asp Arg Trp Trp Trp Trp
  1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic BOC-Phe-Leu-Phe-Leu-Phe-OH

<400> SEQUENCE: 10

Phe Leu Phe Leu Phe
  1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic
      isopropylureido-Phe-Leu-Phe-Leu-Phe-OH

<400> SEQUENCE: 11

Phe Leu Phe Leu Phe
  1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)
<223> OTHER INFORMATION: Xaa can be Asp, Arg or Trp.
<220> FEATURE:
<221> NAME/KEY: PEPTIDE
<222> LOCATION: (2)
<223> OTHER INFORMATION: Xaa can be His, Lys or Arg.

<400> SEQUENCE: 12

Xaa Xaa Arg Trp Trp Met
  1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)
<223> OTHER INFORMATION: Xaa can be Asp, Arg or Trp.
<220> FEATURE:
```

```
<221> NAME/KEY: PEPTIDE
<222> LOCATION: (2)
<223> OTHER INFORMATION: Xaa can be His, Lys or Arg.

<400> SEQUENCE: 13

Xaa Xaa Arg Trp Trp Trp
  1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)
<223> OTHER INFORMATION: Xaa can be Asp, Arg or Trp.
<220> FEATURE:
<221> NAME/KEY: PEPTIDE
<222> LOCATION: (2)
<223> OTHER INFORMATION: Xaa can be His, Lys or Arg.

<400> SEQUENCE: 14

Xaa Xaa Trp Trp Trp Met
  1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)
<223> OTHER INFORMATION: Xaa can be Asp, Arg or Trp.
<220> FEATURE:
<221> NAME/KEY: PEPTIDE
<222> LOCATION: (2)
<223> OTHER INFORMATION: Xaa can be His, Lys or Arg.

<400> SEQUENCE: 15

Xaa Xaa Trp Trp Trp Trp
  1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)
<223> OTHER INFORMATION: Xaa is w or D-Trp while W is L-Trp.

<400> SEQUENCE: 16

Xaa Trp Arg Trp Trp Met
  1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic

<400> SEQUENCE: 17

Trp Trp Arg Trp Trp Trp
```

1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic

<400> SEQUENCE: 18

Trp Trp Arg Trp Trp Met
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)
<223> OTHER INFORMATION: Xaa is w or D-Trp while W is L-Trp.

<400> SEQUENCE: 19

Xaa Trp Arg Trp Trp Trp
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

Trp Trp Trp Trp Trp Met
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic

<400> SEQUENCE: 21

Trp Trp Trp Trp Trp Arg
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic

<400> SEQUENCE: 22

Trp Trp Trp Arg Trp Trp
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic

```
<400> SEQUENCE: 23

Leu Trp Trp Trp Trp Trp
 1               5

<210> SEQ ID NO 24
<211> LENGTH: 4
<212> TYPE: PRT
<213> ORGANISM: Artificial Sequence
<220> FEATURE:
<223> OTHER INFORMATION: Synthetic

<400> SEQUENCE: 24

Arg Trp Trp Trp
 1

<210> SEQ ID NO 25
<211> LENGTH: 4
<212> TYPE: PRT
<213> ORGANISM: Artificial Sequence
<220> FEATURE:
<223> OTHER INFORMATION: Synthetic

<400> SEQUENCE: 25

Arg Trp Trp Met
 1

<210> SEQ ID NO 26
<211> LENGTH: 4
<212> TYPE: PRT
<213> ORGANISM: Artificial Sequence
<220> FEATURE:
<223> OTHER INFORMATION: Synthetic

<400> SEQUENCE: 26

Trp Trp Trp Trp
 1

<210> SEQ ID NO 27
<211> LENGTH: 6
<212> TYPE: PRT
<213> ORGANISM: Artificial Sequence
<220> FEATURE:
<223> OTHER INFORMATION: Synthetic

<400> SEQUENCE: 27

Leu Arg Trp Trp Trp Trp
 1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Trp Trp Trp Trp Arg Trp
 1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic

<400> SEQUENCE: 29
```

```
Trp Trp Trp Trp Met Arg
  1               5

<210> SEQ ID NO 30
<211> LENGTH: 4
<212> TYPE: PRT
<213> ORGANISM: Artificial Sequence
<220> FEATURE:
<223> OTHER INFORMATION: Synthetic

<400> SEQUENCE: 30

Trp Trp Trp Met
  1

<210> SEQ ID NO 31
<211> LENGTH: 6
<212> TYPE: PRT
<213> ORGANISM: Artificial Sequence
<220> FEATURE:
<223> OTHER INFORMATION: Synthetic

<400> SEQUENCE: 31

Trp Trp Trp Trp Trp Trp
  1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (6)
<223> OTHER INFORMATION: Xaa is w or D-Trp while W is L-Trp.

<400> SEQUENCE: 32

Trp Trp Trp Trp Trp Xaa
  1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic

<400> SEQUENCE: 33

Trp Arg Arg Trp Trp Trp
  1               5

<210> SEQ ID NO 34
<211> LENGTH: 4
<212> TYPE: PRT
<213> ORGANISM: Artificial Sequence
<220> FEATURE:
<223> OTHER INFORMATION: Synthetic

<400> SEQUENCE: 34

Trp Arg Trp Trp
  1

<210> SEQ ID NO 35
<211> LENGTH: 4
<212> TYPE: PRT
<213> ORGANISM: Artificial Sequence
<220> FEATURE:
```

```
<223> OTHER INFORMATION: Synthetic
<220> FEATURE:
<221> NAME/KEY: PEPTIDE
<222> LOCATION: (4)
<223> OTHER INFORMATION: Xaa is w or D-Trp while W is L-Trp.

<400> SEQUENCE: 35

Trp Trp Trp Xaa
  1

<210> SEQ ID NO 36
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (4)
<223> OTHER INFORMATION: Xaa is w or D-Trp while W is L-Trp.

<400> SEQUENCE: 36

Arg Trp Trp Xaa
  1
```

US 7,671,028 B2

PEPTIDES THAT ANTAGONIZE FPR CLASS RECEPTOR MEDIATED SIGNALING

The present application is a national phase application of PCT/KR2005/00329, filed Feb. 3, 2005, under 35 U.S.C. 371.

BACKGROUND OF THE INVENTION

1. Field of the Invention

The present invention relates to the discovery of molecules that inhibit an immune or inflammatory response in a subject. The present invention also relates to treating neurodegenerative disease. More specifically, the invention disclosed herein concerns molecules that interact with a FPR class receptor.

2. General Background and State of the Art

The formyl peptide receptor, FPR, class receptors are G-protein-coupled, seven transmembrane receptors that bind the chemoattractant fMLP and are involved in monocyte chemotaxis and the induction of a host immune response to a pathogen. The prototype FPR class receptor, FPR, binds fMLP with high affinity and is activated by low concentrations of fMLP. The binding of FPR by fMLP induces a cascade of G protein-mediated signaling events leading to phagocytic cell adhesion, chemotaxis, release of oxygen intermediates, enhanced phagocytosis and bacterial killing, as well as MAP kinase activation and gene transcription.

Formyl peptide receptor like 1 (FPRL1) is one of the classic chemoattractant receptors, i.e., a G protein-coupled seven trans-membrane receptor. FPRL1 was initially cloned as a formyl peptide receptor (FPR) homolog by low stringency hybridization with the human FPR cDNA probe (1). FPRL1 has 69% sequence identity at the amino acid level with FPR (1). Though FPR expression is restricted to phagocytic cells, FPRL1 is expressed in various cell types, including, phagocytes, epithelial cells, endothelial cells, hepatocytes, and astrocytoma cells (2-5). This broad spectrum of receptor expression indicates that FPRL1 may be involved in the regulation of various cellular responses. FPRL1 has important roles in the regulation of immune responses by modulating the activities of phagocytes (6). As member of a family of FPR that are capable of binding bacterial chemotactic formyl peptides, FPRL1 is regarded to perform a role in the host defense mechanism against pathogen infection (6, 7). In particular, FPRL1 has been reported to mediate phagocyte chemotaxis (8, 9), and the activation of FPRL1 was found to cause superoxide generation and exocytosis in human neutrophils. In terms of the modulation of HIV-1 infection, FPRL1 has been reported to attenuate HIV-1 infection by enhancing innate immunity, and its transition to adaptive immunity, or by desensitizing important chemokine receptors that act as co-receptors of viral infection (10). CCR5 and CXCR4 were desensitized by FPRL1 activation in a phosphorylation-dependent mechanism (10). FPRL1 plays a role not only in the immune system, but also in the neuronal system. FPRL1 has important implications in several disease states, such as in amyloidosis and in neurodegenerative disease (11, 12). FPRL1 was also found to be highly expressed in mononuclear phagocytes that infiltrate the brain tissues of Alzheimer's disease patients (12). FPRL1 is also believed to play a role in the pro-inflammatory aspects of prion disease (13).

Recently, several novel FPRL1 agonists have been identified. They include host-derived agonists, such as LL-37, an enzymatic cleavage fragment of the neutrophil granule-derived cathelicidin, and a mitochondrial peptide fragment MYFINILTL (SEQ ID NO:1) cleaved from NADH dehydrogenase subunit I (8, 14). Some peptides derived from HIV-1 envelope proteins have also been demonstrated to bind FPRL1 (15-17). Among peptides from gp41 of HIV-1, T21/DP107 was found to be a potent ligand for FPRL1 (15). Two different peptides from gp120 named F peptide and V3 peptide are also potent FPRL1 agonists (16, 17). From random peptide libraries Back et al., isolated a potent leukocyte stimulating peptide, Trp-Lys-Tyr-Met-Val-Met-CONH$_2$ (WKYMVM, SEQ ID NO:2), Seo et al., modified by substituting the L-methionine at the C terminus of peptides with D-methionine to produce the more potent ligand, Trp-Lys-Tyr-Met-Val-D-Met-ONH$_2$ (WKYMVm, SEQ ID NO:3) (18, 19). Recently Le et al. demonstrated that WKYMVm (SEQ ID NO:3) is a potent peptide ligand for FPRL1 (20).

For normal physiological responses, phagocytic cells must be recruited into sites of tissue damage. Recruited cells perform key roles against invading pathogens or to remove damaged cells. However, if the recruitment of phagocytic cells into the infection site is excessive, it causes several adverse effects, for example, tissue damage and inflammatory disease (21). Since most agonists induce many cellular signals that modulate complex cellular responses via binding to their specific cell surface receptors, the development of selective antagonists against specific receptors appears to be a sound approach for the generation of anti-inflammatory molecules. In terms of FPRL1, although the receptor plays a critical role in the recruitment of phagocytic cells into an infected area and several FPRL1 agonists have been reported, no antagonists for FPRL1 have been reported. To reveal the role of FPRL1 in physiological and pathological conditions specific FPRL1 antagonists would be highly desirable.

SUMMARY OF THE INVENTION

Among the known ligands for FPRL1, WKYMVm (SEQ ID NO:3) has several merits with respect to FPRL1 antagonist screening. The peptide has potent phagocyte recruiting activity, and it is a small peptide consisting of only 6 amino acids. Peptide antagonists of the classical chemoattractant receptor, FPRL1, were identified by screening hexapeptide libraries to identify peptides that inhibit the binding of iodine-labeled WKYMVm (SEQ ID NO:3) to FPRL1. The peptides blocked FPRL1-induced cellular signaling and cellular responses.

Activation of FPRL1 is closely related to inflammatory responses in the host defense mechanism and neurodegenerative disorders. Among the inventive peptides, Trp-Arg-Trp-Trp-Trp-Trp-ONH$_2$ (WRWWWW, WRW$^4$, (SEQ ID NO:4)), showed the most potent activity in terms of inhibiting WKYMVm (SEQ ID NO:3) binding to FPRL1. WRW$^4$ (SEQ ID NO:4) and wWRWWM (SEQ ID NO:16) inhibited the activation of FPRL1 by WKYMVm (SEQ ID NO:3), resulting in the complete inhibition of intracellular calcium ([Ca$^{2+}$]$_i$) increase. WRW$^4$ (SEQ ID NO:4) also inhibited ERK activation and the chemotactic migration of cells by WKYMVm (SEQ ID NO:3). On the receptor specificity of WRW$^4$ (SEQ ID NO:4) to the FPR family, WRW$^4$ (SEQ ID NO:4) specifically inhibit [Ca$^{2+}$]$_i$ increase by FPRL1 agonists (MMK-1, amyloid β42 (Aβ42) peptide, F peptide) but not by FPR agonist (fMLF). To investigate the effect of WRW$^4$ (SEQ ID NO:4) on endogenous FPRL1 ligand-induced cellular responses, its effect on Aβ42 peptide in human neutrophils was determined. Aβ42 peptide-induced superoxide generation and the chemotactic migration of neutrophils were also inhibited by WRW$^4$ (SEQ ID NO:4), which also completely inhibited the internalization of Aβ42 peptide in human macrophages.

The present invention is directed to a polypeptide comprising a W-rich peptide and a conservative variant or functional fragment thereof. The polypeptide may be from about 4 to 15 amino acids long, from 4 to 10 amino acids long, from 4 to 7 amino acids long or 6 amino acids long. Further, the polypeptide may be represented by SEQ ID NOS:4, 5, 6, 8, 12, 13, 14, 15, 16, 17, 18, 19, 20, 21, 22, 23, 24, 25, 26, 27, 28, 29, 30, 31, 32, 33, 34, 35, 35 or 7. In particular, the polypeptide may be represented by SEQ ID NOS:4, 5, 6, 8, 12, 13, 14, 15, 16, 17, 18, 19, 20, 21, 22, 23, 24, 25, 26, 27, 28, 29 or 30. Further, the polypeptide may be represented by SEQ ID NOS:4, 5, 6, 8, 12, 13, 14, 15, 16, 17, 18, 19, 20, 21, 22, 23, 24, 25, 26 or 27. Even further, the polypeptide may be represented by SEQ ID NOS:4, 16, 17, 18, 19, 20, 21, 22, 23 or 25. Still further, the polypeptide may be represented by SEQ ID NOS:4, 16, 18, 20, 21 or 22. Even further, the polypeptide may be represented by SEQ ID NOS:4, 16, 18 or 20. Further still, the polypeptide may be represented by SEQ ID NOS:4 or 16.

According to another aspect of the invention, a W-rich peptide mimic is also disclosed. In another aspect, the invention is directed to a method of preventing inflammation in a subject comprising the steps of: providing an inflammation preventing effective amount of the polypeptide described above or a W-rich peptide mimic thereof to the subject in need thereof.

In yet another aspect, the invention is directed to a method of treating arthritis in a subject comprising the steps of: providing an inflammation preventing effective amount of the polypeptide described above or a W-rich peptide mimic thereof to the subject in need thereof.

In still another aspect, the invention is directed to a method of treating an auto-immune disease in a subject comprising the steps of: providing a therapeutically effective amount of the polypeptide described above or a W-rich peptide mimic thereof to the subject in need thereof.

In another aspect, the invention is directed to a method of preventing binding of Aβ42 to human neutrophils comprising contacting the neutrophil with the polypeptide described above or a W-rich peptide mimic thereof.

In yet another aspect, the invention is directed to a method of treating Alzheimer's Disease comprising administering a therapeutically effective amount of the polypeptide described above or a W-rich peptide mimic thereof to a subject in need thereof.

In another aspect, the invention is directed to a method of identifying a FPR class receptor antagonist comprising the steps of: providing a cell having a FPR class receptor; contacting the cell with a candidate antagonist compound; and identifying the candidate antagonist compound as an antagonist compound If the candidate binds to a FPR class receptor and inhibits its activity. And the FPR class receptor may be a FPRL1. The invention is further directed to a pharmaceutical composition comprising the polypeptide described above or W-rich peptide mimic thereof.

These and other objects of the invention will be more fully understood from the following description of the invention, the referenced drawings attached hereto and the claims appended hereto.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will become more fully understood from the detailed description given herein below, and the accompanying drawings which are given by way of illustration only, and thus are not limitative of the present invention, and wherein.

DETAILED DESCRIPTION OF THE PREFERRED EMBODIMENTS

Figure 1:
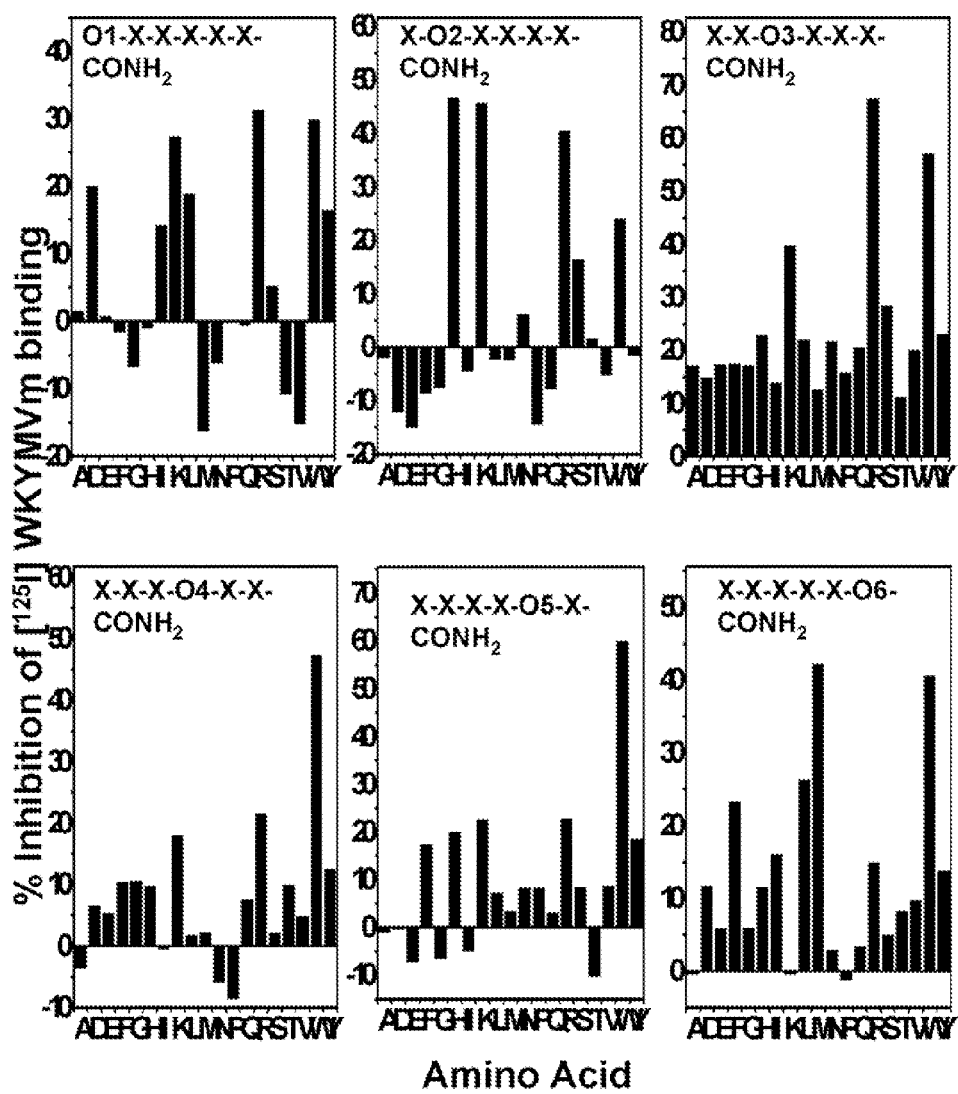
FIG. 1 shows the initial screening of the PS-SPCLs for peptides that inhibit the binding of $^{125}$I-labeled WKYMVm (SEQ ID NO:3) in FPRL1-expressing RBL-2H3 cells. Each panel shows the results obtained with peptide pools of known amino acids at each of the six positions of the hexapeptide. The six positions are individually defined (O1, O2 etc.) by the positioning of one of the 19 L-amino acids. The remaining five positions consist of mixtures (X) of the 19 L-amino acids (except for cysteine). FPRL1-expressing RBL-2H3 cells ($1 \times 10^5$ cells/200 µl) were used for binding assay. The ligand binding assay was monitored as described in the EXAMPLE section. The results shown are representative of four independent experiments.

In the present application, "a" and "an" are used to refer to both single and a plurality of objects.

As used herein, "about" or "substantially" generally provides a leeway from being limited to an exact number. For example, as used in the context of the length of a polypeptide sequence, "about" or "substantially" indicates that the polypeptide is not to be limited to the recited number of amino acids. A few amino acids added to or subtracted from the N-terminus or C-terminus may be included so long as the functional activity such as its binding activity is present.

As used herein, "carriers" include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein, "effective amount" is an amount sufficient to effect beneficial or desired clinical or biochemical results. An effective amount can be administered one or more times. For purposes of this invention, an effective amount of an inhibitor compound is an amount that is sufficient to palliate, ameliorate, stabilize, reverse, slow or delay the progression of the disease state. In a preferred embodiment of the invention, the "effective amount" is defined as an amount of compound capable of preventing binding of a FPR class receptor and its agonist. Preferably, the FPR class receptor is FPRL1.

As used herein, "FPR class receptor antagonist" refers to a compound that specifically and antagonistically binds to a FPR class receptor such as FPRL1, and thus it would be within the purview of a person of skill in the art to make certain variations to the antagonist, which retains the capability of specifically and antagonistically binding to a FPR class receptor.

As used herein, "ligand" refers to any molecule or agent, or compound that specifically binds covalently or transiently to a molecule such as a polypeptide.

As used herein, "mammal" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein, "purified" or "isolated" molecule refers to biological or synthetic molecules that are removed from their natural environment and are isolated or separated and are free from other components with which they are naturally associated.

As used herein, the term "specifically binds" refers to a non-random binding reaction between two molecules, for example between a polypeptide or a peptide mimetic compound that binds to the FPR class receptor.

As used herein, "subject" is a vertebrate, preferably a mammal, more preferably a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

As used herein, "W-rich peptide" refers to an oligopeptide that may be from about 4 to about 15 amino acids long, wherein at least 50% of the amino acid content is tryptophan (both L- and D-forms). Further, the W-rich peptide is an antagonist to the FPR class receptor, and more particularly, the FPRL1 receptor.

Screening for Antagonists that Bind to FPR Class Receptor

In one embodiment, the invention is directed to screening for a compound such as a polypeptide, a peptide mimetic, or chemical compound that inhibits binding of an agonist to FPR class receptor. It is expected that the inhibitor compound will treat persons suffering from diseases that are at least in part caused by the stimulation of the FPR receptor such as neurodegenerative disorders or other general inflammatory conditions.

Various libraries may be used including phage display library or chemical library to screen for compounds that bind to the FPR class receptor and prevent activation by agonists. By another approach, random libraries of molecules are contacted to cells expressing a FPR class receptor and compounds that prevent the agonist activation of FPR class receptor are identified using a variety of assays. Still another approach utilizes two hybrid systems (e.g., yeast or mammalian two-hybrid systems) to identify compounds that reduce immune response of the subject including treating auto-immune disease and to prevent inflammation and disorders that are associated with inflammation such as arthritis, including rheumatoid arthritis and osteoarthritis and further, neurodegenerative disease including Alzheimer's Disease by preventing the activation of FPR class receptors. Many of these approaches are amenable to high throughput analysis. Further, methods are provided that allow for the identification of additional antagonist compounds of FPR class receptors and which further treat and/or prevent autoimmune disease, neurodegenerative disease such as Alzheimer's Disease and prevent or reduce inflammation and disorders that are caused by or are the result of inflammation such as rheumatoid arthritis or osteoarthritis. One approach involves the use of techniques in rational drug design. Accordingly, molecules that resemble identified antagonist compounds, and fragments or derivatives of these molecules, are designed and created using computer based homology searching, protein modeling, and combinatorial chemistry. For example, a database comprising nucleic acid or protein sequences corresponding to W-rich peptide, or fragments or derivatives of these molecules are accessed by a search program that compares the sequence to other sequences in publicly or commercially available databases so as to identify homologous ligands. By another rational approach, techniques in protein modeling (e.g., x-ray crystallography, NMR, and computer modeling) are employed to construct models of the antagonist compounds. From these models, rational drug design can be accomplished. Additionally, protein models comprising FPR class receptors can be created, ligand binding sites can be identified, and this information can be used to rationally design more candidate antagonist compounds.

Once the candidate antagonist compounds are designed and created, it is preferred that they are evaluated for their ability to bind to an FPR class receptor, wherein the antagonist compound prevents the binding by agonist to the FPR class receptor. Approaches that evaluate the ability of a candidate antagonist compound or the antagonist compound to interact with an FPR class receptor thus preventing the activation of FPR class receptor and resultant reduction in inflammation may be carried out using a variety of assays such as chemotaxis assays and $Ca^{+2}$ mobilization assays.

Antagonists that Bind to FPR Class Receptor

In one aspect, the invention is directed to any antagonist molecule that is capable of interacting with FPR class receptor and block the binding of an agonist. It is understood that the antagonist compound may impair the interaction between an agonist and the FPR class receptor (e.g., either FPR and FPRL1) by any number of biochemical or enzymatic inhibition kinetics, such as competitive, non-competitive, or uncompetitive inhibition, so long as the compound impairs the binding of the agonist with the FPR class receptor and prevents activation of the receptor. Exemplified polypeptides include without limitation:

TABLE 1

FPR Class Receptor Antagonists

Antagonist

| | | | | | | |
|---|---|---|---|---|---|---|
| W | R | W | W | W | W | (SEQ ID NO:4) |
| R | R | W | W | W | W | (SEQ ID NO:5) |
| R | H | W | W | W | W | (SEQ ID NO:6) |
| D | R | W | W | W | W | (SEQ ID NO:8) |
| (D/R/W) | (H/K/R) | R | W | W | M | (SEQ ID NO:12) |
| (D/R/W) | (H/K/R) | R | W | W | W | (SEQ ID NO:13) |
| (D/R/W) | (H/K/R) | W | W | W | M | (SEQ ID NO:14) |
| (D/R/W) | (H/K/R) | W | W | W | W | (SEQ ID NO:15) |
| W | W | R | W | W | M | (SEQ ID NO:16) |
| W | W | R | W | W | W | (SEQ ID NO:17) |
| W | W | R | W | W | M | (SEQ ID NO:18) |
| W | W | R | W | W | W | (SEQ ID NO:19) |
| W | W | W | W | W | M | (SEQ ID NO:20) |
| W | W | W | W | W | R | (SEQ ID NO:21) |
| W | W | W | R | W | W | (SEQ ID NO:22) |
| L | W | W | W | W | W | (SEQ ID NO:23) |
| | | R | W | W | W | (SEQ ID NO:24) |
| | | R | W | W | M | (SEQ ID NO:25) |
| | | W | W | W | W | (SEQ ID NO:26) |
| L | R | W | W | W | W | (SEQ ID NO:27) |
| W | W | W | W | R | W | (SEQ ID NO:28) |
| W | W | W | W | M | R | (SEQ ID NO:29) |
| | | W | W | W | M | (SEQ ID NO:30) |
| W | W | W | W | W | W | (SEQ ID NO:31) |
| W | W | W | W | W | w | (SEQ ID NO:32) |
| W | R | R | W | W | W | (SEQ ID NO:33) |
| | | W | R | W | W | (SEQ ID NO:34) |
| | | W | W | W | w | (SEQ ID NO:35) |

TABLE 1-continued

FPR Class Receptor Antagonists

| Antagonist | | | | |
|---|---|---|---|---|
| R | W | W | w | (SEQ ID NO:36) |
| | W | R | W | (SEQ ID NO:7) |

"W" represents L-amino acid;
"w" represents D-amino acid.

Variant and Mutant Polypeptides

By enhancing or inhibiting ("modulating") the induction of an FPR class receptor, cellular responses such as signal transduction, leukocyte migration, immune system response, and inflammatory response can be selectively altered. Embodiments of the invention include the use of molecules that modulate the induction of an FPR class receptor. Throughout this disclosure, the term "FPR class receptor" refers to receptors that can be activated by fMLP and have at least 80% homology to FPR and/or FPRL1.

To improve or alter the characteristics of the antagonist polypeptide, amino acid engineering may be employed. Recombinant DNA technology known to those skilled in the art can be used to create novel mutant polypeptides including single or multiple amino acid substitutions, deletions, additions, or fusion proteins. Similar mutant polypeptides can also be produced by chemical synthesis, especially for short peptides. Such modified polypeptides can show, e.g., increased/decreased activity or increased/decreased stability. In addition, they may be purified in higher yields and show better solubility than the corresponding natural polypeptide, at least under certain purification and storage conditions.

The antagonist compounds resembling W-rich peptide, and fragments or derivatives of these molecules (e.g., W-rich peptide mimics) not only include those molecules containing as a primary amino acid sequence all or part of the amino acid sequence of W-rich peptide, and fragments or derivatives of these molecules found in nature but also altered sequences in which functionally equivalent amino acid residues are substituted for residues within the sequence resulting in a silent change. Accordingly, one or more amino acid residues within the sequence of W-rich peptide, and fragments or derivatives of these molecules can be substituted by another amino acid of a similar polarity that acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan, and methionine. The uncharged polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. The aromatic amino acids include phenylalanine, tryptophan, and tyrosine. In other aspects of the invention, W-rich peptide, and fragments or derivatives of these molecules, which are differentially modified during or after translation, e.g., by phosphorylation, glycosylation, cross-linking, acylation, proteolytic cleavage, linkage to an antibody molecule, membrane molecule, or other ligand, are contemplated.

Accordingly, the protein sequence corresponding to W-rich peptide, or a fragment or derivative of these molecules can be compared to known sequences. The candidate antagonist compounds can have the following degrees of homology to W-rich peptide, for example: 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. The candidate antagonist compounds having greater than or equal to 50% homology are identified and are subsequently examined using a antagonist compound characterization assay. Antagonist compounds that can prevent the agonist activation of a FPR class receptor, especially FPRL1 receptor and thereby treat and/or prevent auto-immune disease, or neurodegenerative disease, or prevent or reduce inflammation and various disorders that are associated with it can then be identified.

Mimetics

Peptides for use in aspects of the invention can also be modified, e.g., the peptides can have substituents not normally found on a peptide or the peptides can have substituents that are normally found on the peptide but are incorporated at regions of the peptide that are not normal. The peptides for use in aspects of the invention can be acetylated, acylated, or aminated, for example. Substituents which can be included on the peptide so as to modify it include, but are not limited to, H, alkyl, aryl, alkenyl, alkynl, aromatic, ether, ester, unsubstituted or substituted amine, amide, halogen or unsubstituted or substituted sulfonyl or a 5 or 6 member aliphatic or aromatic ring. As used throughout this disclosure, the term "antagonist compound", "antagonist agent" or "antagonist peptide" can refer to a modified or unmodified peptide and a chemical or a peptidomimetic that structurally (three-dimensionally or two-dimensionally) resembles a modified or unmodified W-rich peptide, and fragments or derivatives of these molecules. A "W-rich peptide mimic" is an antagonist compound that resembles the W-rich peptide. W-rich peptide mimics can be peptidomimetics, peptides, modified peptides, and derivatized peptides and thus, are members of the class of antagonist compounds.

Additional antagonist compound derivatives include peptidomimetics that resemble a polypeptide of interest. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Synthetic compounds that mimic the conformation and desirable features of a particular peptide, e.g., an oligopeptide, once such peptide has been found, but that avoids the undesirable features, e.g., flexibility (loss of conformation) and bond breakdown are known as "peptidomimetics".

In general, the design and synthesis of a peptidomimetic involves starting with the sequence of the peptide and the conformation data (e.g., geometry data, such as bond lengths and angles) of a desired peptide (e.g., the most probable simulated peptide), and using such data to determine the geometries that should be designed into the peptidomimetic. Numerous methods and techniques are known in the art for performing this step, any of which could be used. (See, e.g., Farmer, P. S., Drug Design, (Ariens, E. J. ed.), Vol. 10, pp. 119-143 (Academic Press, New York, London, Toronto, Sydney and San Francisco) (1980); Kemp, D. S., "Peptidomimetics and the Template Approach to Nucleation of .beta.-sheets and alpha.-helices in Peptides," Tibech, Vol. 8, pp. 249-255 (1990).

In one embodiment, a peptide mimetic is defined as a non-peptide ligand that is recognized by a peptide recognition site. Such mimetics may be structurally different from the peptides. A well-known example of a peptide mimetic is morphine. This natural opioid alkaloid is a mimetic of β-endorphin, a peptide present in the human body. While this definition of a peptide mimetic characterizes a mimetic as a non-peptide ligand, many structures exist that are somewhere in between a true peptide, which is composed of natural amino acids, and a peptide mimetic. Most compounds within the spectrum of the definition are considered peptide mimetics as well. For example, a tripeptide composed exclusively of non-natural elements can be considered a peptide mimetic. Several HIV protease inhibitors are considered peptide mimetics, although they possess amide bonds and amino acids. The debate on what constitutes a peptide mimetic is still on-going, however a person of skill in the art is able to distinguish between a mimetic and a peptide. Peptide mimetics can generally be considered as improved versions of peptides. Chemical modifications on a peptide, such as the reduction of a peptide bond, can increase its enzymatic stability. Incorporating unnatural amino acids can also enhance both activity and selectivity of the peptide. The more a peptide is altered structurally and/or chemically, the more it becomes a true peptide mimetic. Peptide mimetics including peptides, proteins, and derivatives thereof, such as peptides containing non-peptide organic moieties, synthetic peptides which may or may not contain amino acids and/or peptide bonds, but retain the structural and functional features of a peptide ligand, and peptoids and oligopeptoids which are molecules comprising N-substituted glycine, such as those described by Simon et al., Proc. Natl. Acad. Sci. USA 89:9367 (1992); and antibodies, including anti-idiotype antibodies.

In another aspect of the invention, the inventive compound of the invention may be made by synthetically introducing a variety of optional compounds, such as scaffolds, turn mimetics, and peptide-bound replacements. Syntheses of amino acids to the use of a variety of linear and heterocyclic scaffolds in place of the peptide backbone may be used. Chemical procedures and methods include the transient protection of charged peptides as neutral prodrugs for improved blood-brain penetration and the replacement of peptide bonds with groups such as heterocyclic rings, olefins and fluoroolefins, and ketomethylenes.

In an embodiment of the invention, the mimetic is highly specific to its target and has low toxicity and is directed to peptide mimetics that cross the blood-brain barrier so as to antagonize the binding of beta-amyloid protein with FPR class receptor in the brain. Therefore, an inhibitor compound that is modified so that the compound is able to cross the cell membrane barrier, as well as the blood-brain barrier is encompassed by the present invention.

Therapeutic Composition

The discovery of several new antagonist compounds for FPR class receptors is provided in this disclosure. These pharmaceuticals can be delivered by any conventional route including, but not limited to, transdermal, topical, parenteral, gastrointestinal, transbronchial, and transalveolar. A preferred application concerns the use of the antagonist compounds in a coating for medical devices. Embodiments of the invention also include biotechnological tools, prophylactics, therapeutics, and methods of use of the foregoing, for the study, treatment, and/or prevention of auto-immune disease, neurodegenerative disease such as Alzheimer's Disease and prevention and/or reduction of inflammation as well as prevention and/or treatment of disorders associated with inflammation such as rheumatoid arthritis and osteoarthritis.

In one embodiment, the present invention relates to treatment for various diseases that are characterized by the activation of FPR class receptor. FPR receptor is known to be activated in inflammatory conditions and in neurodegenerative diseases such as Alzheimer's disease where the plaque protein Aβ42 protein is an agonist for FPRL1. In this way, the inventive therapeutic compound may be administered to human patients who are either suffering from, or prone to suffer from a neurogenerative disease by providing compounds that inhibit the various agonists for FPR class receptor. In particular, the disease is associated with dementia, chronic neurodegenerative disorder of the brain, loss of nerve cell, particularly in the hippocampus and cerebral cortex, reduced neurotransmitters, cerebrovascular degeneration, and/or loss of cognitive ability. Further in particular, the present invention is directed to a treatment for Alzheimer's Disease. Preferably, the compound crosses the blood-brain barrier. Further, the present invention is also directed to therapeutic compounds for the treatment of other disorders associated with activation of FPR class receptor or FPRL1 receptor, including without limitation, auto-immune disease and inflammation and disorders related to inflammation such as rheumatoid arthritis and osteoarthritis.

Methods of reducing inflammation and methods of ameliorating or preventing neurodegenerative disease and methods of treating or preventing auto-immune disease are also embodiments of the invention. Accordingly, a method of reducing inflammation involves identifying a subject in need of a compound that interacts with an FPR class receptor and providing the subject with a therapeutically sufficient amount of the W-rich peptide or a fragment, derivative, modification or mimic thereof. A method of preventing or ameliorating neurodegenerative disease according to one aspect of the invention, involves identifying a subject at risk for developing a neurodegenerative disease such as Alzheimer's Disease, or a subject already afflicted with a neurodegenerative disease and providing the subject with a therapeutically sufficient amount of an antagonist compound for a FPR class receptor such as a W-rich peptide or mimic thereof.

The formulation of therapeutic compounds is generally known in the art and reference can conveniently be made to Remington's Pharmaceutical Sciences, 17th ed., Mack Publishing Co., Easton, Pa., USA. For example, from about 0.05 μg to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intradermal or suppository routes or implanting (eg using slow release molecules by the intraperitoneal route or by using cells e.g. monocytes or dendrite cells sensitised in vitro and adoptively transferred to the recipient). Depending on the route of administration, the peptide may be required to be coated in a material to protect it from the action of enzymes, acids and other natural conditions which may inactivate the ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique, which yield a powder of the active ingredient plus any additional desired ingredient from a previously sterile-filtered solution thereof.

When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutically active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µg to about 2000 mg. Expressed in proportions, the active compound is generally present in from about 0.5 µg/ml of carrier. In the case of compositions containing supplementary active ingredients, the dosages are determined by reference to the usual dose and manner of administration of the ingredients.

Delivery Systems

Various delivery systems are known and can be used to administer a compound of the invention, e.g., encapsulation in liposomes, microparticles, microcapsules, receptor-mediated endocytosis. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, the implant being of a porous, non-porous, or gelatinous material, including membranes, such as sialastic membranes, or fibers. Preferably, when administering a protein, including a peptide or peptide mimetic compound of the invention, care must be taken to use materials to which the protein does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, i.e., the brain, thus requiring only a fraction of the systemic dose.

A composition is said to be "pharmacologically or physiologically acceptable" if its administration can be tolerated by a recipient subject and is otherwise suitable for administration to that subject. Such an agent is said to be administered in a "therapeutically effective amount" if the amount administered is physiologically significant. An agent is physiologically significant if its presence results in a detectable change in the physiology of a recipient patient.

FPRL1 Antagonists and W-Rich Peptides

W-rich peptide, and fragments or derivatives of these molecules can be provided to a subject in need thereof to treat and prevent auto-immune disease, neurodegenerative disease and prevent or reduce inflammation and disorders related to it. Chemicals and peptidomimetics that resemble FPR class receptor antagonists or fragments thereof and protease stable derivatives of the FPR class receptor antagonists or fragments thereof can also be used to treat and prevent auto-immune disease, neurodegenerative disease and prevent or reduce inflammation and related disorders.

In the present application, the W-rich peptide has been exemplified as hexapeptides. However, the application is not limited to hexapeptides. The peptide may be slightly longer or slightly shorter. The peptide may be in the range of 4 to 15 amino acids long, preferably 4 to 10 amino acids, preferably 4 to 7 or about 6 amino acids, so long as the peptide antagonizes formyl peptide receptor like-1-mediated signaling.

Further, the W-rich peptide of the invention has at least about 50% tryptophan (W-L-amino acid form and/or w-D-amino acid form) content in the peptide. Preferably, the tryptophan content is at least about 60%, 62%, 65%, 66%, 67%, 70%, 75%, 77%, 80%, 85%, 88%, 90%, 95% or 100%.

By screening peptide libraries several hexapeptides were identified, which antagonize FPRL1 signaling. W-rich peptides such as WRW$^4$ (SEQ ID NO:4), RHW$^4$ (SEQ ID NO:6), RRW$^4$ (SEQ ID NO:5), and DRW$^4$ (SEQ ID NO:8) were found to interact directly with FPRL1 and to inhibit the binding of WKYMVm (SEQ ID NO:3) to its cell surface receptor in a concentration-dependent manner. Moreover, WRW$^4$ (SEQ ID NO:4) exerted an antagonistic effect on WKYMVm (SEQ ID NO:3)-induced FPRL1 signaling, and blocked not only chemotactic migration but also the superoxide generated by Aβ42 peptide in human neutrophils.

Figure 2:
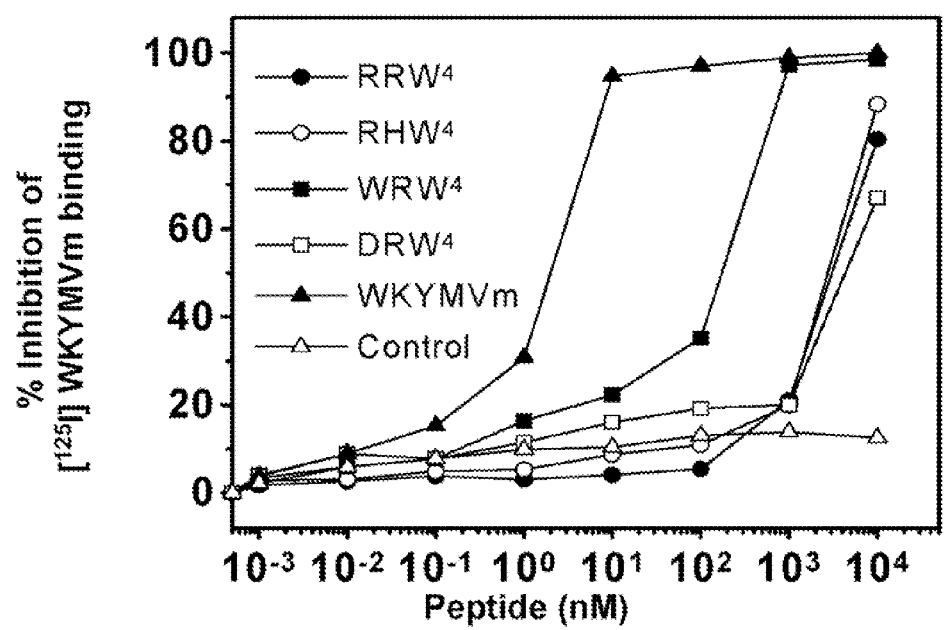
FIG. 2 shows effect of several candidate peptides based on the PS-SPCL screening results with regard to the inhibition of WKYMVm (SEQ ID NO:3) binding in FPRL1-expressing RBL-2H3 cells. FPRL1-expressing RBL-2H3 cells ($1 \times 10^5$ cells/200 µl) were used for binding assay, and various concentrations of each unlabeled peptide (RRWWWW, RRW$^4$ (SEQ ID NO:5); RHWWWW, RHW$^4$ (SEQ ID NO:6); WRWWWW, WRW$^4$ (SEQ ID NO:4); DRWWWW, DRW$^4$ (SEQ ID NO:8)) were pretreated prior to the addition of $^{125}$I-labeled WKYMVm (SEQ ID NO:3) (50 pM). Specifically bound $^{125}$I-labeled WKYMVm (SEQ ID NO:3) was measured. The results shown are representative of four independent experiments.
Figure 3:
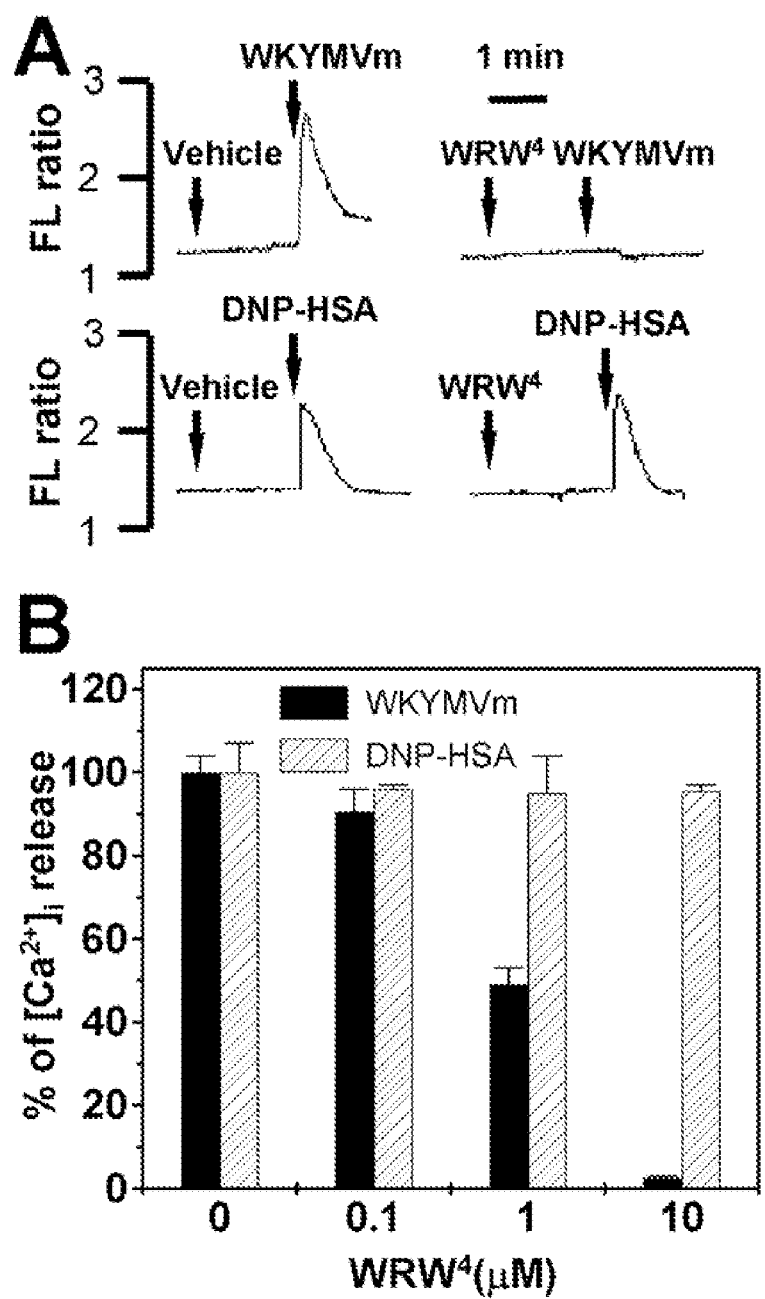
FIGS. 3A-3B show effects of WRW$^4$ (SEQ ID NO:4) on the WKYMVm (SEQ ID NO:3)-induced $[Ca^{2+}]_i$ rise in FPRL1 expressing RBL-2H3 cells. Fura-2-loaded FPRL1-expressing RBL-2H3 cells were stimulated with vehicle or WRW$^4$ (SEQ ID NO:4) (10 µM) and then with WKYMVm (SEQ ID NO:3) (10 nM); or FPRL1-expressing RBL-2H3 cells were sensitized with DNP-specific IgE, loaded with fura-2, and activated with the antigen DNP-HSA (1 µg/ml). The changes in 340 nm/380 nm were monitored. The results are representative of three independent experiments (A). Cells were stimulated with various concentrations of WRW$^4$ (SEQ ID NO:4) prior to adding 10 nM of WKYMVm (SEQ ID NO:3) or 1 µg/ml of DNP-HSA. Peak levels of $[Ca^{2+}]_i$ increase were monitored. The results shown are the means±SE of four independent experiments (B).
Figure 4:
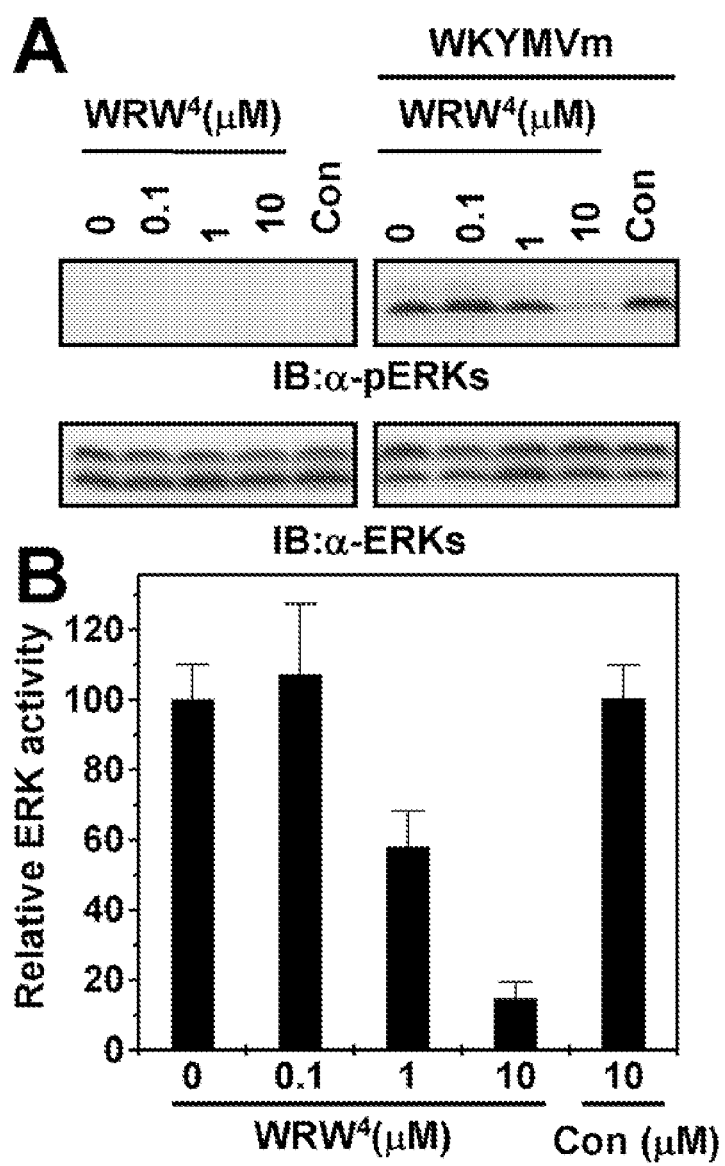
FIGS. 4A-4B show effects of WRW$^4$ (SEQ ID NO:4) on the WKYMVm (SEQ ID NO:3)-stimulated ERK activation in FPRL1-expressing RBL-2H3 cells. FPRL1-expressing RBL-2H3 cells were treated with various concentrations of WRW$^4$ (SEQ ID NO:4) for 5 min (A, left), and then stimulated with various concentrations of WRW$^4$ (SEQ ID NO:4) or 10 µM control peptide, LFMYHP (SEQ ID NO:9), for 1 min prior to the addition of vehicle or 10 nM WKYMVm (SEQ ID NO:3) for 5 min (A, right). Each sample (30 µg of protein) was subjected to 8% SDS-PAGE and phosphorylated ERK was determined by immunoblot analysis with anti-phospho-ERK antibody (A). ERK phosphorylation was quantified by densitometry. Results are presented as the means ±SE of 5 independent experiments (B).

In the process of immuno-modulating activity of chemoattractants, it is important to induce phagocytic cell accumulation into infected tissues (6, 7). Although the excessive recruitment of phagocytic cells causes adverse effects, such as inflammatory response, few have reported upon the possible negative regulation of chemoattractant-induced responses. The direct negative regulation of chemoattractant signaling can be induced by interrupting agonist-receptor binding. This study shows that a number of W-rich peptides blocked WKYMVm (SEQ ID NO:3) binding to FPRL1 (FIG. 2). In terms of the peptide, WRW$^4$ (SEQ ID NO:4), we found that it blocked all the tested cellular activities induced by WKYMVm (SEQ ID NO:3) investigated in FPRL1-expressing RBL-2H3 cells. Specifically, WRW$^4$ (SEQ ID NO:4) blocked WKYMVm (SEQ ID NO:3)-induced $[Ca^{2+}]_i$ increase, ERK activation, and chemotactic migration (FIGS. 2, 3, and 4). Taken together, these findings show that WRW$^4$ (SEQ ID NO:4) blocks WKYMVm (SEQ ID NO:3)-initiated FPRL1-signaling by blocking the binding of WKYMVm (SEQ ID NO:3) to the receptor. As FPRL1 is an important chemoattractant receptor, which is involved in the host defense mechanism against pathogen infections, W-rich peptides will be useful agents for the development of anti-inflammatory drugs. wWRWWM (SEQ ID NO:16) is also a potent antagonist, which even more powerfully blocked WKYMVm (SEQ ID NO:3)-induced $[Ca^{2+}]_i$ increase than WRW$^4$ (SEQ ID NO:4).

Figure 6:
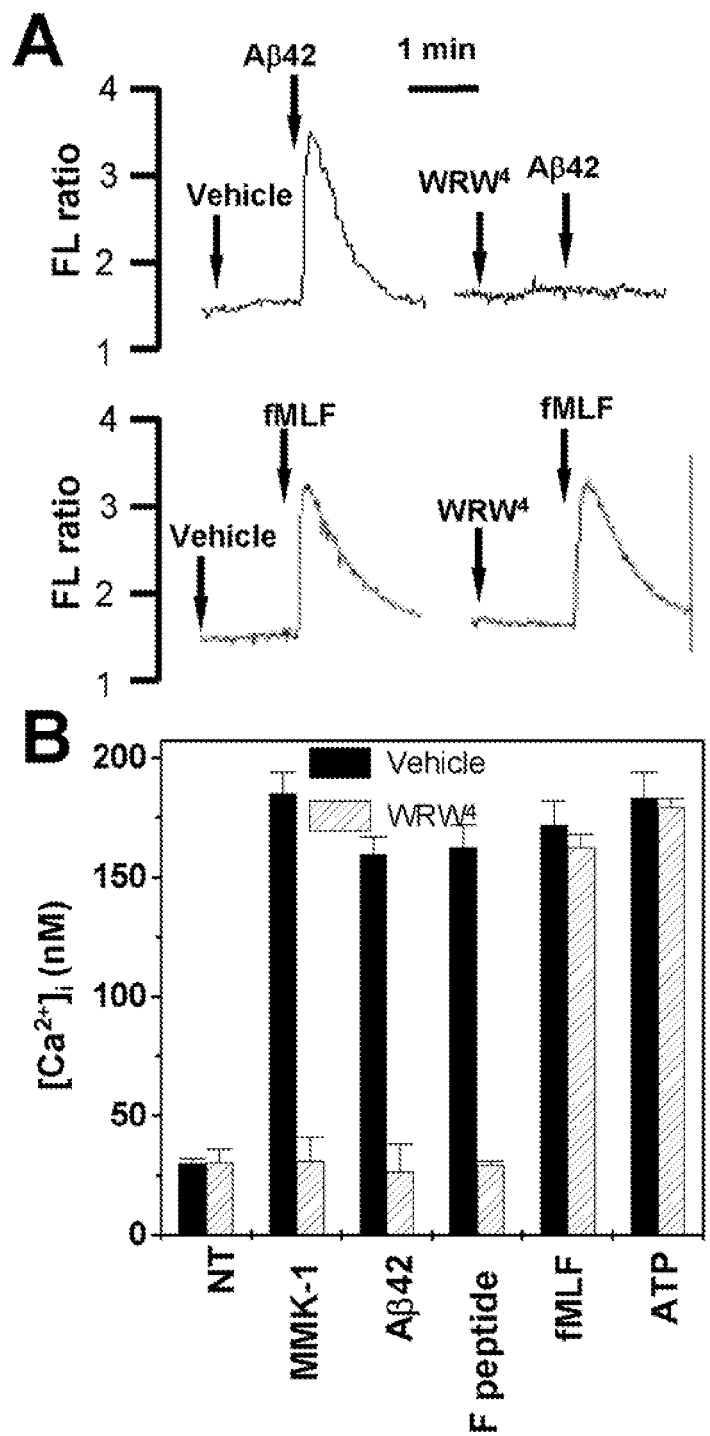
FIGS. 6A-6B show specific inhibition of FPRL-1-induced [Ca$^{2+}$]$_i$ rise by WRW$^4$ (SEQ ID NO:4) in human neutrophils. Fura-2-loaded human neutrophils were treated with vehicle or WRW$^4$ (SEQ ID NO:4) (10 µM), then stimulated with Aβ42 (40 µM) or fMLF (1 µM). Changes in 340 nm/380 nm were monitored. The results shown are representative of three independent experiments (A). Neutrophils were stimulated with vehicle or WRW$^4$ (SEQ ID NO:4) (10 µM), then stimulated with MMK-1 (1 µM), Aβ42 (40 µM), F peptide (30 µM), fMLF (1 µM), or ATP (500 µM) (B). Changes in 340 nm/380 nm were monitored and the calibrated fluorescence ratio was converted to [Ca$^{2+}$]$_i$. Results are presented as means±SE of three independent experiments each performed in duplicate (B).

Due to the significant role of FPR family receptors in inflammatory responses, many research groups have tried to identify receptor antagonists for the receptor family. To date, a few antagonists for FPR have been reported (30-32). Two FPR antagonists (tBOC-Phe-Leu-Phe-Leu-Phe-OH (SEQ ID NO:10) and isopropylureido-Phe-Leu-Phe-Leu-Phe-OH (SEQ ID NO:11)), which has $IC_{50}$ values in the range of 0.44-3.7 μM, have been developed by replacement of the formyl group of fMLF with t-butyloxylcarbonyl (tBOC) or isopropylureido group (30, 31). A cyclic undecapeptide, cyclosporine H (CsH) has been developed as a potent and selective FPR antagonist (32). CsH has been reported to inhibit FPR-mediated $Ca^{2+}$ mobilization, chemotaxis, and release of proinflammatory mediators (32-34). Even though some FPR-specific antagonists have been developed and investigated their putative role as therapeutic agents for modulators of inflammatory responses, FPRL1-specific antagonists have not been reported until now. Several synthetic hexapeptides that act as FPRL1 antagonists are disclosed herein. In particular, WRW$^4$ (SEQ ID NO:4) specifically inhibited all the tested FPRL1 agonists (MMK-1, Aβ42 peptide, and F peptide)-induced $[Ca^{2+}]_i$ increase but not fMLF-induced one (FIG. 6), and further, the peptide is used to create improved FPR class receptor specific or FPRL-1 specific antagonist.

Figure 7:
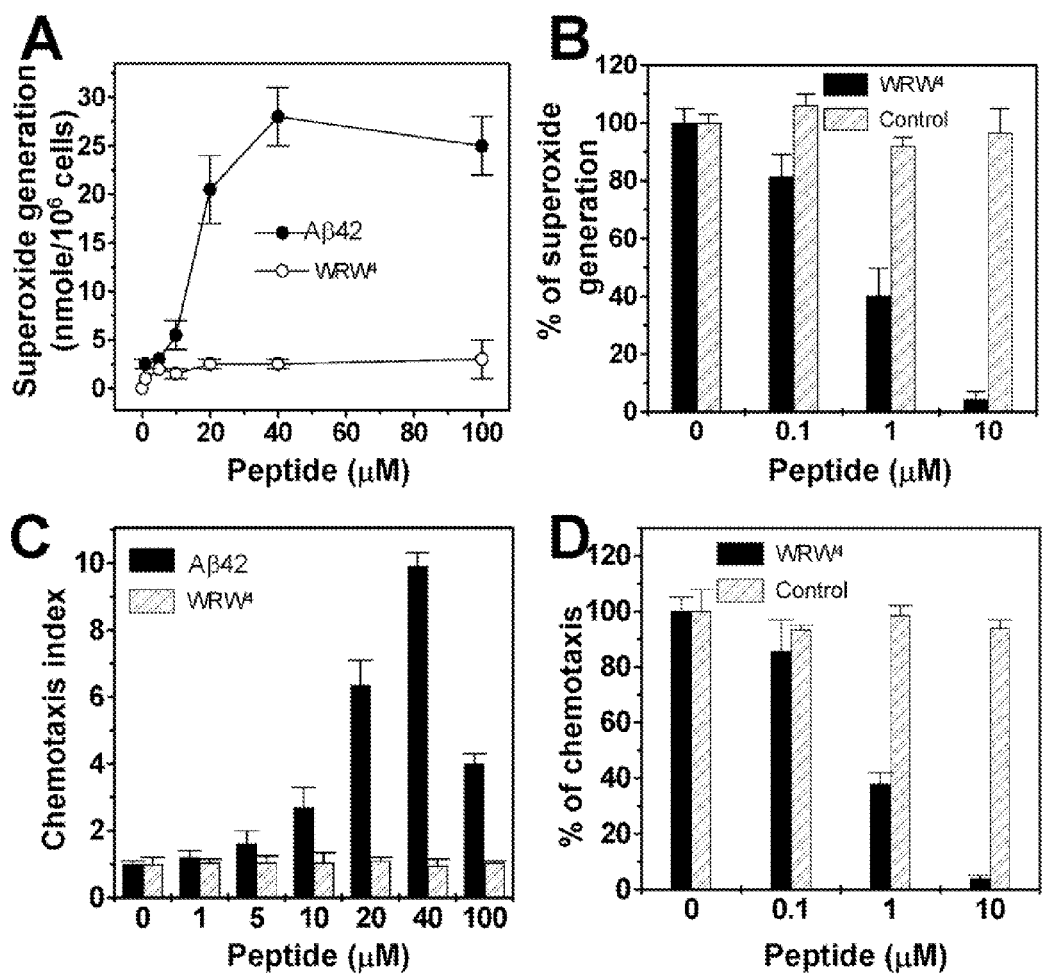
FIGS. 7A-7D show effects of WRW$^4$ (SEQ ID NO:4) on the Aβ42-induced superoxide generation and chemotaxis in human neutrophils. Human neutrophils (1×10$^6$ cells/100 µl) were stimulated with various concentrations of WRW$^4$ (SEQ ID NO:4) or Aβ42 (A). Cells were preincubated with several concentrations of WRW$^4$ (SEQ ID NO:4) or with 10 µM of control peptide (LFMYHP, SEQ ID NO:9) for 1 minute prior to adding 40 µM of Aβ42 peptide (B). Cytochrome c reduction was monitored, as described in EXAMPLES. The results shown are representative of four independent experiments (A, B). Chemotaxis assays were performed using a modified Boyden chamber assay, as described in EXAMPLES. Various concentrations of WRW$^4$ (SEQ ID NO:4) or Aβ42 were used for the assay (C). Several concentrations of WRW$^4$ (SEQ ID NO:4) or 10 µM of the control peptide (LFMYHP, SEQ ID NO:9) were pretreated prior to the chemotaxis assay using 40 µM Aβ42 (D). The data are presented as mean±SE of three independent experiments each performed in duplicate (C, D).

Previous reports have shown that inflammation is critically involved in the pathogenesis of Alzheimer's disease (35). Moreover, Aβ42 peptide is one of the enzymatic cleavage fragments of amyloid precursor protein (36), and has been reported to play a significant role in the proinflammatory responses of systemic amyloidosis, such as Alzheimer's disease (35, 36). Recently, Aβ42 peptide was found to bind to FPRL1 and to modulate the generation of reactive oxygen species and cellular chemotactic migration in human neutrophils via FPRL1 (29). FIG. 7 demonstrates that preincubation of human neutrophils with WRW$^4$ (SEQ ID NO:4) prior to Aβ42 peptide treatment caused complete inhibition of Aβ42 peptide-induced neutrophil chemotaxis and ROS generation.

Figure 8:
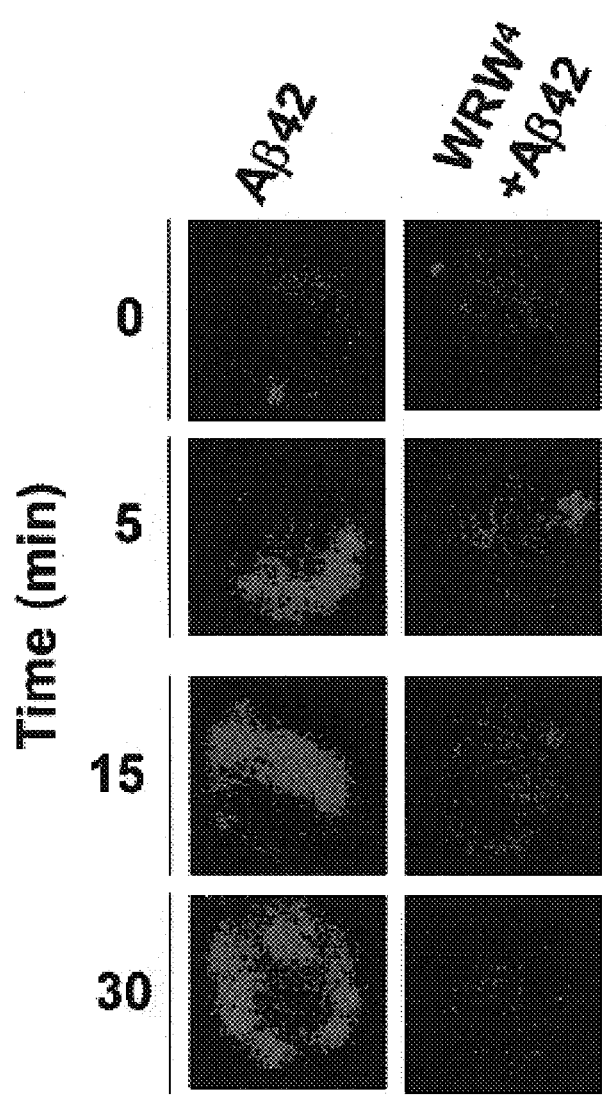
FIG. 8 shows effect of WRW$^4$ (SEQ ID NO:4) on the internalization of Aβ42 peptide in human macrophages. Human macrophages were cultured on chamber slides and incubated with 10 µM of Aβ42 at 37° C. for various times in the absence or presence of 10 µM of WRW$^4$ (SEQ ID NO:4). The cells were then rinsed, permeabilized, and stained with anti-Aβ42 antibody. The samples were further incubated with FITC conjugated goat anti-mouse IgG. Aβ42 staining was examined under a confocal microscope.

In terms of Alzheimer's disease, Aβ42 peptide is known to play a central role in mediating neurotoxicity and in the formation of senile plaques (35, 36). It has been reported that mononuclear phagocytes in the brain express FPRL1, and that FPRL1 gene expression is elevated in CD11b-positive mononuclear phagocytes that infiltrate senile plaques in the brain tissues of Alzheimer's disease patients (12). Aβ42 peptide also has been reported to increase neurodestructive reactive oxygen species and reactive nitrogen and tumor necrosis factor α in brain microglia cells and in peripheral blood mononuclear phagocytes (37). These molecules are elevated in Alzheimer's disease (35-37). More recently, Yazawa et al. reported that Aβ42 peptide is internalized via FPRL1 and forms fibrillar aggregates in macrophages (27). It is disclosed herein that WRW$^4$ (SEQ ID NO:4) is an FPRL1-specific antagonist, which blocks the internalization of Aβ42 peptide in human macrophages (FIG. 8). Thus, WRW$^4$ (SEQ ID NO:4) provides a developmental basis of a drug that blocks the internalization of Aβ42 peptide and fibrillar formation.

In addition to Aβ42 peptide, several other ligands, derived from the HIV-1 envelope domains or host-derived agonists, have been reported to bind to FPRL1 (14-17). Further studies are needed to evaluate the effect of WRW$^4$ (SEQ ID NO:4) on other FPRL1 agonist-related cellular responses and diseases. Although WRW$^4$ (SEQ ID NO:4) was found to inhibit the activation of FPRL1 by WKYMVm (SEQ ID NO:3) and by Aβ42, work is required to investigate the effect of WRW$^4$ (SEQ ID NO:4) on the activation of FPRL1 by other FPRL1 agonists. In summary, an antagonist to FPR class receptor, in particular the FPRL1 receptor such as WRW$^4$ (SEQ ID NO:4), is developed as a useful molecule for producing drug for the treatment of several diseases in which FPRL1 is known to play a role.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Materials and Methods for FPRL1 Antagonist Peptide Characterization 1.1 Materials Fmoc amino acids were obtained from Millipore (Bedford, Mass.). Rapidamide resin from Dupont (Boston, Mass.); peripheral blood mononuclear cell separation medium (Histopaque-1077) and cytochrome c from Sigma (St. Louis, Mo.); fura-2 pentaacetoxymethylester (fura-2/AM) from Molecular Probes (Eugene, Oreg.); RPMI 1640 from Invitrogen Corp. (Carlsbad, Calif.) and dialyzed fetal bovine serum and supplemented bovine serum from Hyclone Laboratories Inc. (Logen, Utah). Radioiodinated WKYMVm (SEQ ID NO:3) ($^{125}$I-labeled) was a gift from Amersham Pharmacia Biotech (Buckinghamshire, UK). Amyloid β42 (Aβ42) was purchased from Bachem Bioscience (King of Prussia, Pa.); anti-phospho-ERK antibodies and anti-ERK antibodies from Cell Signaling Technology, Inc. (Beverly, Mass.), and Anti-Aβ42 antibody from Zymed Laboratories, Inc. (South San Francisco, Calif.).

1.2 Positional Scanning Synthetic Peptide Combinatorial Libraries (PS-SPCLs)

The hexapeptide libraries were prepared by the Peptide Library Support Facility of Pohang University of Science and Technology, as described previously (18, 19). Finally, 114 peptide pools (Cys was excluded in the construction of the libraries) were individually dissolved in water at a final concentration of 27 nM per peptide sequence in each peptide pool. Peptides were synthesized using a previously described solid-phase method (18). Briefly, peptides were synthesized on a Rapidamide support resin and assembled by following the standard Fmoc/t-butyl strategy on an acid-labile linker. Peptide compositions were confirmed by amino acid analysis as previously described (18, 19).

1.3 Cell culture

FPRL1-expressing RBL-2H3 cells and vector-transfected RBL-2H3 cells were maintained as previously described (22). Cells were maintained at about $1\times10^6$ cells/ml under standard incubator conditions (humidified atmosphere, 95% air, 5% $CO_2$, 37° C.). Peripheral blood was collected from healthy donors, and human neutrophils were isolated by dextran sedimentation, hypotonic lysis of erythrocytes and lymphocyte separation medium gradient, as previously described (23). Isolated human neutrophils were promptly separated using a medium gradient, as described previously (23), and isolated human leukocytes were used promptly. Peripheral blood mononuclear cells were isolated by separation on a Histopaque-1077 gradient. After two washings with Hank's buffered saline solution (HBSS), without $Ca^{2+}$ and $Mg^{2+}$, PBMCs were suspended in RPMI medium containing 10% FBS and incubated for 60 min at 37° C. to allow monocytes attachment to the culture dish. Attached monocytes were then collected as described previously (23). Peripheral blood monocytes were differentiated to macrophages by culturing the cells on 4-well chamber slides (Nalge Nunc International, Rochester, N.Y.) in RPMI 1640 medium containing 0.1% bovine serum albumin, 0.01M HEPES (pH 7.4), and 20 ng/ml monocyte colony stimulating factor (PeproTech, Rocky Hill, N.J.).

1.4 Screening of Peptide Libraries and Ligand Binding Analysis

For the initial screening of the positional scanning synthetic peptide combinatorial libraries (PS-SPCLs), we measured the effect of each peptide pool on the binding of $^{125}$I-WKYMVm (SEQ ID NO:3) to its specific receptor, FPRL1 in RBL-2H3 cells. Ligand binding analysis was performed as previously described (24). Briefly, FPR-expressing RBL-2H3 cells were seeded at $1\times10^5$ cells per well into a 24 well plate and cultured overnight. After blocking the cells with blocking buffer (33 mM HEPES, pH 7.5, 0.1% BSA in RPMI) for 2 hr, 50 pM of labeled WKYMVm (SEQ ID NO:3) was added to the cells in binding buffer (PBS containing 0.1% BSA), in the absence or presence of unlabelled peptides (final 0.5 nM per peptide sequence for the initial screening), and then incubated for 3 hr at 4° C. with continuous shaking. The samples were then washed 5 times with ice-cold binding buffer, and 200 µl of lysis buffer (20 mM Tris, pH 7.5, 1% Triton X-100) was added to each well. After 20 min at room temperature, the lysates were collected and counted using a γ-ray counter (24).

1.5 Measurement of Intracellular Calcium Concentration

Intracellular calcium concentration ($[Ca^{2+}]_i$) levels were determined by Grynkiewicz's method using fura-2/AM (25). Briefly, prepared cells were incubated with 3 µM fura-2/AM at 37° C. for 50 min in fresh serum free RPMI 1640 medium with continuous stirring. For DNP-HSA stimulation, RBL-2H3 cells were sensitized with 1 µg/ml mouse DNP-specific IgE overnight prior to fura-2 loading (26), and $2 \times 10^6$ cells were aliquoted for each assay in $Ca^{2+}$ free Locke's solution (154 mM NaCl, 5.6 mM KCl, 1.2 mM $MgCl_2$, 5 mM HEPES, pH 7.3, 10 mM glucose, and 0.2 mM EGTA). The fluorescence changes at excitation wavelengths of 340 nm and 380 nm and a common emission wavelength of 500 nm were measured, and the calibrated fluorescence ratio was converted to $[Ca^{2+}]_i$.

1.6 Stimulation of Cells with Peptides for Western Blot Analysis

FPRL1-expressing RBL-2H3 cells or isolated human neutrophils ($2 \times 10^6$) were stimulated with the indicated concentrations of peptides for predetermined times. After stimulation, the cells were washed with serum free RPMI and lysed in lysis buffer (20 mM Hepes, pH 7.2, 10% glycerol, 150 mM NaCl, 1% Triton X-100, 50 mM NaF, 1 mM $Na_3VO_4$, 10 µg/ml leupeptin, 10 µg/ml aprotinin, and 1 mM phenylmethylsulfonyl fluoride). Detergent insoluble materials were pelleted by centrifugation (12,000×g, 15 min, at 4° C.), and the soluble supernatant fraction was removed and stored at either −80° C. or used immediately. Protein concentrations in the lysates were determined using Bradford protein assay reagent.

1.7 Electrophoresis and Western Blot Analysis

Proteins were separated in 8% SDS-polyacrylamide gel and, the proteins were blotted onto a nitrocellulose membrane, which was then blocked by incubating with TTBS (Tris-buffered saline, 0.05% Tween-20) containing 5% nonfat dry milk. Subsequently, membranes were incubated with specific antibodies and washed with TBS. Antigen-antibody complexes were visualized after incubating the membrane with 1:5000 diluted goat anti-rabbit IgG or goat anti-mouse IgG antibody coupled to horseradish peroxidase and detected by enhanced chemiluminescence.

1.8 Chemotaxis Assay

Chemotaxis assays were performed using multiwell chambers (Neuroprobe Inc., Gaithersburg, Md.) (23). Briefly, polycarbonate filters (8 µm pore size) were precoated with 50 µg/ml of rat type I collagen (Collaborative Biomedicals) in HEPES-buffered RPMI 1640 medium. A dry coated filter was placed on a 96-well chamber containing different concentrations of peptides. RBL-2H3 cells expressing FPRL1 were then suspended in RPMI at a concentration of $1 \times 10^6$ cells/ml, and then, 25 µl of the suspension were placed onto the upper well of the chamber. After incubating for 4 hr at 37° C., non-migrated cells were removed by scraping, and cells that had migrated across the filter were dehydrated, fixed, and stained with hematoxylin (Sigma, St. Louis, Mo.). Stained cells in five randomly chosen high power fields (HPF) (400×) were then counted. For the neutrophil chemotaxis assay, prepared human neutrophils were suspended in RPMI at a concentration of $1 \times 10^6$ cells/ml, and 25 µl of the suspension was placed into the upper well of a chamber, which was separated by 3 µm filter not coated with polyvinylpyrrolidone, for 90 minutes (23).

1.9 Measurement of Superoxide Generation

Superoxide anion generation was determined by measuring cytochrome c reduction using a microtiter 96 well plate ELISA reader (Bio-Tekinstruments, EL312e, Winooski, Vt.) as previously described (23). Human neutrophils ($1 \times 10^6$ cells/100 µl of RPMI 1640 medium per well of a 96-well plate) were preincubated with 50 µM cytochrome c at 37° C. for 1 min and then incubated with the indicated concentrations of peptides. Superoxide generation was determined for the change in light absorption at 550 nm over 5 minutes at 1 min intervals.

1.10 Fluorescence Confocal Microscopy

Confocal microscopic analysis using anti-Aβ42 antibody was performed, as described before (27). Briefly, human macrophages grown on 4-well chamber slides were treated with 10 µM of Aβ42 peptide in the absence or presence of 10 µM WRWWWW (SEQ ID NO:4) for different periods at 37° C. The cells were then fixed in 4% paraformaldehyde for 10 minutes at room temperature, washed with PBS and incubated with 5% goat serum (Sigma) in PBS containing 0.05% Tween-20 for 1 hr, to block nonspecific binding and permeabilization. Samples were then incubated with anti-Aβ42 antibody for 1 hr at room temperature, slides were washed three times with PBS, and incubated with FITC-conjugated goat anti-mouse IgG (Sigma, 1:500 in TBS containing 3% BSA) for 30 min. Mounted samples were observed under a laser scanning confocal fluorescence microscope (Zeiss).

Example 2

Results of FPRL1 Antagonist Peptide Characterization 2.1 Identification of Peptides that Inhibit the Binding of WKYMVm (SEQ ID NO:3) to FPRL1

In this study, a total of 114 peptide pools (around 47 million peptides) from hexapeptide PS-SPCLs were screened to identify peptides that inhibit the binding of WKYMVm (SEQ ID NO:3) to its cell surface receptor. FIG. 1 shows the results of the initial screening. We observed that amino acids at different positions induced different levels of inhibition of WKYMVm (SEQ ID NO:3) binding to FPRL1. The most active peptides and position were as follows: Lys (K), Arg(R), or Trp(W) in the 1st position, H is (H), Lys(K), or Arg(R) in the 2nd, Arg(R) or Trp (W) in the 3rd, Trp (W) in the 4th, Trp (W) in the 5th, and Met (M), or Trp (W) in the $6^{th}$ position of hexapeptides.

Based on the results of the 1st screening of the peptide libraries, we generated, by reiterative synthesis, 4 peptide pools each containing $3 \times 3 \times 1 \times 1 \times 1 \times 1 = 9$ individual hexapeptides. Each peptide mixture contained (D/R/W)(H/K/R)RWWM (SEQ ID NO:12), (D/R/W)(H/K/R)RWWW (SEQ ID NO:13), (D/R/W)(H/K/R)WWWM (SEQ ID NO:14), or (D/R/W)(H/K/R)WWWW (SEQ ID NO:15). The effect of each peptide mixture was examined on the binding of labeled WKYMVm (SEQ ID NO:3) to FPRL1. A peptide mixture with the sequence (D/R/W)(H/K/R)WWWW (SEQ ID NO:15) showed greatest activity in terms of competing with WKYMVm (SEQ ID NO:3) binding to FPRL1 (data not shown). The peptide mixture was purified into 4 fractions by reverse-phase HPLC using a C18 column (Vydac, 218TP1022, 22×250 mm). The effectiveness of the peptides at inhibiting WKYMVm (SEQ ID NO:3) binding to FPRL1 in RBL-2H3 cells was evaluated using the method described for the initial screening. Peptides within the fraction with greatest activity were identified by mass spectrometry. After confirming the effects of the synthesized single peptides on the inhibition of labeled WKYMVm (SEQ ID NO:3), we finally identified Trp-Arg-Trp-Trp-Trp-Trp-CONH$_2$ (WRW-WWW, WRW$^4$ (SEQ ID NO:4)), Arg-His-Trp-Trp-Trp-Trp-CONH$_2$ (RHWWWW, RHW$^4$ (SEQ ID NO:6)), Asp-Arg-Trp-Trp-Trp-Trp-CONH$_2$ (DRWWWW, DRW$^4$ (SEQ ID NO:8)) and Arg-Arg-Trp-Trp-Trp-Trp-CONH$_2$ (RRW-WWW, RRW$^4$ (SEQ ID NO:5)) as being the most active peptide in terms of inhibiting the binding of WKYMVm (SEQ ID NO:3) to FPRL1 in RBL-2H3 cells. The inhibitory effects of the four hexapeptides were tested at several concentrations (FIG. 2). The peptide WRW$^4$ (SEQ ID NO:4) was found to most effectively inhibit $^{125}$I-WKYMVm (SEQ ID NO:3) binding. Three other peptides RHW$^4$ (SEQ ID NO:6), DRW$^4$ (SEQ ID NO:8), and RRW$^4$ (SEQ ID NO:5) also effectively inhibited the binding of labeled WKYMVm (SEQ ID NO:3) binding (FIG. 2). As a negative control experiment, we confirmed that the random sequence of the hexapeptide (Leu-Phe-Met-Tyr-His-Pro-CONH$_2$, LFMYHP (SEQ ID NO:9)) caused no inhibitory effect at up to 10 μM (FIG. 2). The IC$_{50}$ values for the inhibition of $^{125}$I-WKYMVm (SEQ ID NO:3) binding to FPRL1 were 0.23 μM for WRW$^4$ (SEQ ID NO:4), 3.2 μM for RHW$^4$ (SEQ ID NO:6), 2.4 μM for RRW$^4$ (SEQ ID NO:5), and 3.4 μM for DRW$^4$ (SEQ ID NO:8).

2.2 WRW$^4$ (SEQ ID NO:4) Inhibited [Ca$^{3+}$]$_i$ Increase by Activating FPRL1

The stimulation of FPRL1 by WKYMVm (SEQ ID NO:3) elicited a [Ca$^{2+}$]$_i$ increase in FPRL1-expressing RBL-2H3 cells (FIG. 3A). To investigate whether the inventive peptides inhibited WKYMVm (SEQ ID NO:3)-induced [Ca$^{2+}$]$_i$ increase, we stimulated fura-2 loaded FPRL1-expressing RBL-2H3 cells with various concentrations of WRW$^4$ (SEQ ID NO:4), and subsequently stimulated with effective concentration of WKYMVm (SEQ ID NO:3). As shown in FIG. 3A, 10 μM WRW$^4$ (SEQ ID NO:4) alone did change the intracellular calcium concentration. However, 10 μM WRW$^4$ (SEQ ID NO:4) pretreatment prior to stimulation with 10 nM WKYMVm (SEQ ID NO:3) completely inhibited the [Ca$^{2+}$]$_i$ increase induced by WKYMVm (SEQ ID NO:3) in FPRL1-expressing RBL-2H3 cells (FIG. 3A). To confirm specific inhibition by WRW$^4$ (SEQ ID NO:4) on FPRL1-induced signaling, we examined the effect of WRW$^4$ (SEQ ID NO:4) on another extracellular signal-induced [Ca$^{2+}$]$_i$ increase. FcεRI cross-linking has been reported to induce a [Ca$^{2+}$]$_i$ increase in RBL-2H3 cells (26). Stimulation of FPRL1-expressing RBL-2H3 cells (sensitized with 1 μg/ml mouse DNP-specific IgE) with 1 μg/ml DNP-HSA caused a dramatic increase in [Ca$^{2+}$]$_i$ (FIG. 3A). However, pretreatment with 10 μM WRW$^4$ (SEQ ID NO:4) prior to DNP-HSA stimulation did not significantly change the DNP-HSA-induced [Ca$^{2+}$]$_i$ increase in RBL-2H3 cells (FIG. 3A). These results indicate that the WRW$^4$ (SEQ ID NO:4)-induced inhibition of [Ca$^{2+}$]$_i$ increase is a FPRL1-specific event. On examining the concentration-dependency of the WRW$^4$ (SEQ ID NO:4)-induced inhibition of [Ca$^{2+}$]$_i$ increase by WKYMVm (SEQ ID NO:3), we observed that WRW$^4$ (SEQ ID NO:4) inhibited the WKYMVm (SEQ ID NO:3)-mediated process in a concentration-dependent manner, showing maximal inhibition at 10 μM (FIG. 3B); 1 μM WRW$^4$ (SEQ ID NO:4) inhibited WKYMVm (SEQ ID NO:3)-induced [Ca$^{2+}$]$_i$ increase by around 55% (FIG. 3B). These results strongly suggest that WRW$^4$ is a specific antagonist of FPRL1.

2.3 WRW$^4$ Inhibits ERK Activation by FPRL1

To support our notion that WRW$^4$ (SEQ ID NO:4) peptide antagonizes FPRL1 signaling, we examined its effect on WKYMVm (SEQ ID NO:3)-induced ERK activation. Thus, we stimulated FPRL1-expressing RBL-2H3 cells with various concentrations of WRW$^4$ (SEQ ID NO:4) and measured the ERK phosphorylation level by Western blot with anti-phospho-ERK antibody. As shown in FIG. 4A, WRW$^4$ (SEQ ID NO:4) alone did not affect ERK activity in the cells. However, when we stimulated the cells with 10 nM of WKYMVm (SEQ ID NO:3) for 2 min, we observed a dramatic increase in the ERK phosphorylation level (FIG. 4A). Moreover, pretreatment with WRW$^4$ (SEQ ID NO:4) inhibited WKYMVm (SEQ ID NO:3)-elicited ERK phosphorylation in a concentration-dependent manner (FIG. 4A). And, a pretreatment with an inactive control peptide LFMYHP (SEQ ID NO:9) did not inhibit ERK phosphorylation event induced by WKYMVm (SEQ ID NO:3) (FIG. 4A). In addition, we confirmed that same amounts of proteins were used for this experiment by Western blot with anti-ERK antibody (FIG. 4A). FIG. 4B shows the quantitative inhibitory effect of WRW$^4$ (SEQ ID NO:4) in terms of ERK activation by WKYMVm (SEQ ID NO:3). These results indicate that WRW$^4$ (SEQ ID NO:4) blocked [Ca$^{2+}$]$_i$ increase and ERK activation downstream of FPRL1 by WKYMVm (SEQ ID NO:3).

2.4 WRW$^4$ (SEQ ID NO:4) Inhibits FPRL1-Mediated Cellular Chemotaxis

Figure 5:
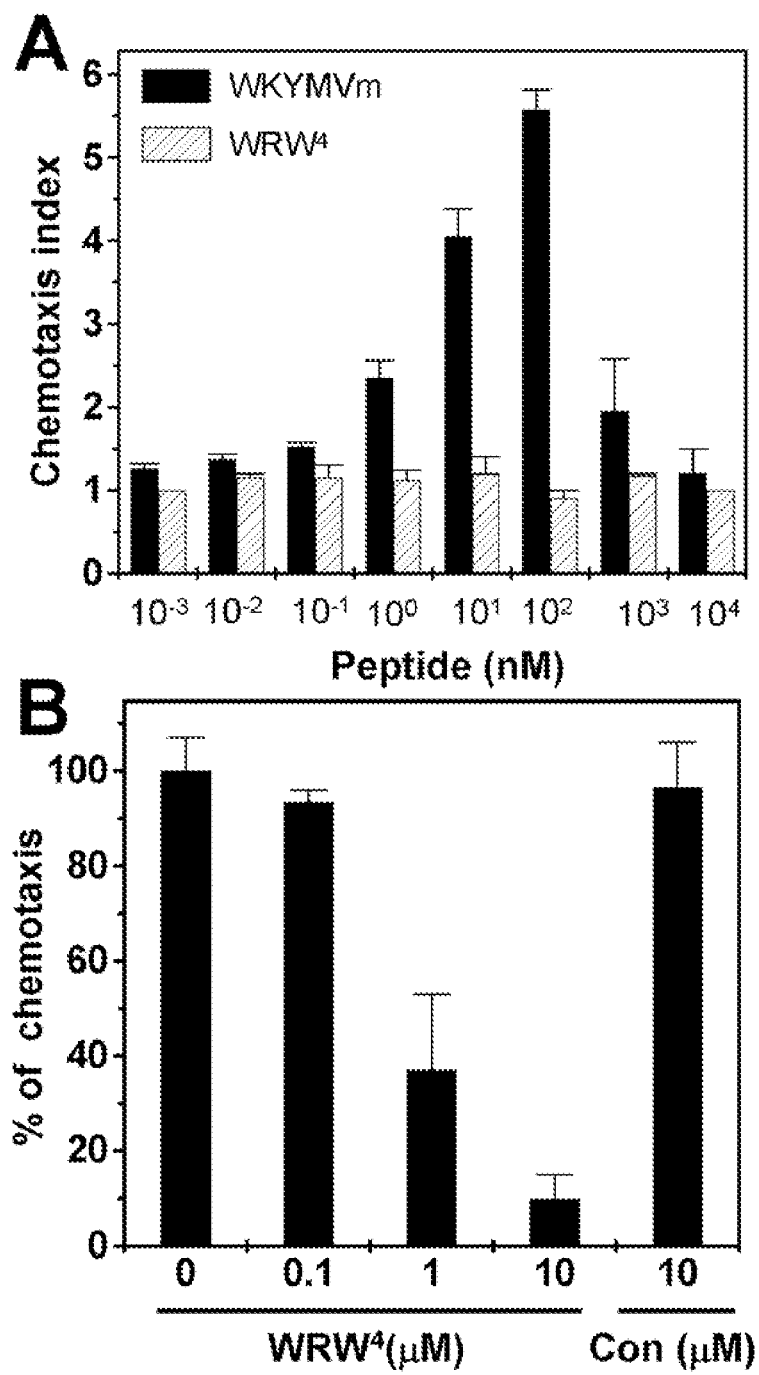
FIGS. 5A-5B show effects of WRW$^4$ (SEQ ID NO:4) on the WKYMVm (SEQ ID NO:3)-induced cellular chemotaxis in FPRL1-expressing RBL-2H3 cells. Assays were performed using a modified Boyden chamber assay, as described in the EXAMPLES. Cultured FPRL1-expressing RBL-2H3 cells ($1 \times 10^6$ cells/ml of serum free RPMI) were added to the upper wells of a 96-well chemotaxis chamber and migration across a polycarbonate membrane of pore size 8 µm was assessed after incubating for 4 hrs at 37° C. Numbers of migrated cells were determined by counting in a high power field (400×). Various concentrations of WRW$^4$ (SEQ ID NO:4) or WKYMVm (SEQ ID NO:3) were used in the assays (A). Several concentrations of WRW$^4$ (SEQ ID NO:4) or 10 µM of LFMYHP (SEQ ID NO:9) were added prior to the chemotaxis assay using 10 nM WKYMVm (SEQ ID NO:3) (B). Results are presented as means±SE of three independent experiments each performed in duplicate.

FPRL1 is a classical chemoattractant receptor, and a previous report demonstrated that WKYMVm (SEQ ID NO:3) induces cellular chemotaxis via FPRL1 (20), which is one of the more important physiological roles of FPRL1. Thus, we investigated the effect of the inventive FPRL1 antagonist WRW$^4$ (SEQ ID NO:4) on WKYMVm (SEQ ID NO:3)-induced chemotaxis, by examining the effect of WRW$^4$ (SEQ ID NO:4) alone on the chemotaxis of FPRL1-expressing RBL-2H3 cells at various peptide concentrations. As shown in FIG. 5A, WKYMVm (SEQ ID NO:3) caused cellular chemotaxis in FPRL1-expressing RBL-2H3 cells in a bell-shaped concentration-dependent manner. However, WRW$^4$ (SEQ ID NO:4) alone showed no effect on cellular chemotaxis at concentrations of 1 nM-10 μM in FPRL1-expressing RBL-2H3 cells (FIG. 5A). We, then, checked the effect of WRW$^4$ (SEQ ID NO:4) on WKYMVm (SEQ ID NO:3)-induced cellular chemotaxis in FPRL1-expressing RBL-2H3 cells, and found that the addition of several concentrations of WRW$^4$ (SEQ ID NO:4) prior to chemotaxis assay using 10 nM WKYMVm (SEQ ID NO:3) caused a concentration-dependent inhibition of WKYMVm (SEQ ID NO:3)-induced chemotaxis of the cells (FIG. 5B). 1 μM WRW$^4$ (SEQ ID NO:4) blocked ca. 60% of WKYMVm (SEQ ID NO:3)-induced chemotaxis and 10 μM WRW$^4$ (SEQ ID NO:4) almost completely blocked WKYMVm (SEQ ID NO:3)-induced this process (FIG. 5B). The addition of 10 μM of an inactive control peptide LFMYHP (SEQ ID NO:9) did not affect WKYMVm (SEQ ID NO:3)-induced chemotaxis (FIG. 5B). These results demonstrate that WRW$^4$ (SEQ ID NO:4) blocks WKYMVm (SEQ ID NO:3)-induced chemotaxis.

2.5 WRW$^4$ (SEQ ID NO:4) Specifically Inhibits FPRL1-Induced Cell Signaling in Human Neutrophils The effect of WRW$^4$ (SEQ ID NO:4) on endogenous ligand-induced FPRL1 signaling was investigated in human neutrophils. Aβ42 peptide has previously been reported to act as an endogenous ligand for FPRL1 (12). We found that treatment of human neutrophils with 40 μM Aβ42 peptide dramatically changes $[Ca^{2+}]_i$ (FIG. 6A), and that WRW[4] (SEQ ID NO:4) alone did not affect this $[Ca^{2+}]_i$ increase in human neutrophils (FIG. 6A). However, when the neutrophils were pretreated with 10 μM of WRW[4] (SEQ ID NO:4) prior to stimulation with 40 μM of Aβ42 peptide, this Aβ42 peptide-induced $[Ca^{2+}]_i$ increase was completely inhibited (FIG. 6A). To determine the specificity of WRW[4] (SEQ ID NO:4) on FPRL1 signaling, we examined the effect of WRW[4] (SEQ ID NO:4) on fMLF-stimulated $[Ca^{2+}]_i$ increase in human neutrophils. Stimulation with 1 μM of fMLF caused a transient $[Ca^{2+}]_i$ increase, but the preincubation of human neutrophils with 10 μM WRW[4] (SEQ ID NO:4) had no affect on the $[Ca^{2+}]_i$ increase by fMLF (FIG. 6A). We also tested the effect of WRW[4] (SEQ ID NO:4) on other FPRL1-specific agonists (MMK-1 and F peptide)-induced $[Ca^{2+}]_i$ increase. As shown in FIG. 6B, 10 μM of WRW[4] (SEQ ID NO:4) prior to stimulation with 1 μM of MMK-1 and 30 μM F peptide, $[Ca^{2+}]_i$ increase by the two FPRL1 agonists was completely inhibited. Stimulation with 500 μM of ATP caused a transient $[Ca^{2+}]_i$ increase, but the preincubation of human neutrophils with 10 μM WRW[4] (SEQ ID NO:4) had no affect on the $[Ca^{2+}]_i$ increase by ATP (FIG. 6B). These results indicate that WRW[4] (SEQ ID NO:4) specifically inhibits FPRL1-induced cell signaling but not FPR-induced one in human neutrophils.

2.6 WRW[4] (SEQ ID NO:4) Inhibits Aβ42 Peptide-Induced Neutrophil Activation

Superoxide generation is one of the important functions of phagocytic leukocytes like neutrophils (28). In this study, we found that Aβ42 increased superoxide generation in human neutrophils. Moreover, this Aβ42 peptide-induced superoxide generating activity was concentration-dependent and showed maximal effect at a peptide concentration of 40 μM (FIG. 7A). The addition of WRW[4] (SEQ ID NO:4) to human neutrophils at up to 100 μM did not affect on the superoxide generation (FIG. 7A). However, when neutrophils were preincubated with various concentrations of WRW[4] (SEQ ID NO:4), Aβ42 peptide-induced superoxide generation was inhibited in a concentration-dependent manner (FIG. 7B), e.g., 10 μM of WRW[4] (SEQ ID NO:4) almost completely inhibited superoxide production by Aβ42 peptide (FIG. 7B). As a control experiment, we examined the effect of inactive control peptide (LFMYHP (SEQ ID NO:9)) on Aβ42 peptide-induced superoxide generation in human neutrophils. Preincubation with several concentrations of LFMYHP (SEQ ID NO:9) prior to Aβ42 peptide stimulation did not affect Aβ42 peptide-stimulated superoxide generation in human neutrophils (FIG. 7B). It has been reported that Aβ42 peptide induces chemotactic migration in human neutrophils via activation of FPRL1 (29). Thus, we examined the effect of Aβ42 on neutrophil chemotaxis, and found that Aβ42 peptide induces neutrophil chemotaxis in a concentration-dependent manner (FIG. 7C). 40 μM of Aβ42 induced 10-fold increase in the number of migrated cells (FIG. 7C). WRW[4] (SEQ ID NO:4) alone did not affect neutrophil chemotaxis between 1 μM-100 μM (FIG. 7C). Thus, to investigate the effect of WRW[4] (SEQ ID NO:4) on Aβ42 peptide-induced neutrophil chemotaxis, we pretreated human neutrophils with several concentrations of WRW[4] (SEQ ID NO:4) prior to the chemotaxis assay with 40 μM of Aβ42. Preincubation of neutrophils with WRW[4] (SEQ ID NO:4) was found to inhibit Aβ42 peptide-induced neutrophil chemotaxis in a concentration-dependent manner (FIG. 7D), and 10 μM of WRW[4] (SEQ ID NO:4) almost completely inhibited the neutrophil chemotaxis induced by Aβ42 peptide (FIG. 7D). Moreover, the control peptide, LFMYHP (SEQ ID NO:9) did not affect on Aβ42 peptide-induced neutrophil chemotaxis (FIG. 7D). These results demonstrate that the selective FPRL1 antagonist, WRW[4] (SEQ ID NO:4), inhibits two important Aβ42 peptide-induced cellular responses, namely, superoxide generation and chemotactic migration in human neutrophils.

2.7 WRW[4] (SEQ ID NO:4) Inhibits Internalization of Aβ42 Peptide in Human Macrophages Aβ42 peptide has been reported to internalize via FPRL1 in human macrophages (27). Since WRW[4] (SEQ ID NO:4) was found to inhibit the intracellular signaling induced by Aβ42 peptide in human neutrophils, we examined the effect of WRW[4] (SEQ ID NO:4) on the internalization of Aβ42. When 10 μM of Aβ42 peptide was incubated in human macrophages, Aβ42 internalization was induced in a time-dependent manner (FIG. 8). Aβ42 peptide internalization occurred from 5 min showing maximal internalization at 30 min after incubation (FIG. 8). When human macrophages were pretreated with 10 μM WRW[4] (SEQ ID NO:4) prior to Aβ42 peptide incubation, we observed that Aβ42 peptide internalization was completely inhibited by WRW[4] (SEQ ID NO:4) (FIG. 8). This result indicates that the preoccupation of FPRL1 by WRW[4] (SEQ ID NO:4) inhibits Aβ42 peptide internalization via FPRL1 in human macrophages.

Example 3

Additional FPRL1 Antagonist Peptide Characterization 3.1—Additional Peptides Inhibited FPRL1-Mediated $[Ca^{2+}]_i$ Increase Methods and principles of assaying for the effects of a set of diverse peptides on the intracellular concentration of calcium when the peptides are contacted with the cells bearing FPRL1 before the FPRL1 agonist is added is described in Example 1.5 above, and further details of initial experimentation using the peptides is described in Example 2.2. The $[Ca^{2+}]_i$ values obtained for the set of antagonist peptides used in this experiment are set forth in Table 2.

In Example 2.2 above, the peptide WRWWWW was indicated to possess a high antagonistic effect on the FPRL1 receptor. However, comparing the values obtained with WRWWWW (SEQ ID NO:4) and other antagonists of this experiment, it can be seen that one peptide, wWRWWM (SEQ ID NO:16) has about a 100 times greater antagonistic activity in terms of the inhibitory effect of the peptide on intracellular calcium concentration increase. Compare their IC50 values at 8.2±0.6 nM for wWRWWM (SEQ ID NO:16) vs. 1000±210 nM for WRWWWW (SEQ ID NO:4).

TABLE 2

Summary of FPRL-1 Antagonist Effect on Intracellular Calcium Content

| Antagonist | | | | | | $Ca^{2+}$ (FPRL1) IC50 (nM) |
|---|---|---|---|---|---|---|
| w | W | R | W | W | M (SEQ ID NO:16) | 8.2 ± 0.6 |
| W | W | R | W | W | W (SEQ ID NO:17) | 58 ± 31 |
| W | W | R | W | W | M (SEQ ID NO:18) | 83 ± 22 |
| w | W | R | W | W | W (SEQ ID NO:19) | 110 ± 29 |

TABLE 2-continued

Summary of FPRL-1 Antagonist Effect on Intracellular Calcium Content

| Antagonist | | | | | | | $Ca^{2+}$ (FPRL1) IC50 (nM) |
|---|---|---|---|---|---|---|---|
| W | W | W | W | W | M | (SEQ ID NO:20) | 130 ± 15 |
| W | W | W | W | W | R | (SEQ ID NO:21) | 220 ± 25 |
| W | W | W | R | W | W | (SEQ ID NO:22) | 470 ± 100 |
| L | W | W | W | W | W | (SEQ ID NO:23) | 500 ± 120 |
|   | R | W | W | W | W | (SEQ ID NO:24) | 600 ±180 |
|   | R | W | W | W | M | (SEQ ID NO:25) | 650 ± 120 |
|   |   | W | W | W | W | (SEQ ID NO:26) | 860 ± 180 |
| W | R | W | W | W | W | (SEQ ID NO:4) | 1000 ± 210 |
| L | R | W | W | W | W | (SEQ ID NO:27) | 1100 ± 940 |
| W | W | W | W | R | W | (SEQ ID NO:28) | 2700 |
| W | W | W | W | M | R | (SEQ ID NO:29) | 5700 |
|   | W | W | W | W | M | (SEQ ID NO:30) | 5900 ± 230 |
| W | W | W | W | W | W | (SEQ ID NO:31) | >10000 |
| W | W | W | W | W | w | (SEQ ID NO:32) | >10000 |
| W | R | R | W | W | W | (SEQ ID NO:33) | >10000 |
|   | W | R | W | W | W | (SEQ ID NO:34) | >10000 |
|   | W | W | W | W | w | (SEQ ID NO:35) | >10000 |
|   | R | W | W | W | w | (SEQ ID NO:36) | >10000 |
|   |   | W | R | W | W | (SEQ ID NO:7) | >10000 |

REFERENCES

Murphy, P. M., T. Ozcelik, R. T. Kenney, H. L. Tiffany, D. McDermott, and U. Francke. 1992. A structural homologue of the N-formyl peptide receptor. Characterization and chromosome mapping of a peptide chemoattractant receptor family. *J. Biol. Chem.* 267: 7637.

Prossnitz, E. R., and R. D. Ye. 1997. The N-formyl peptide receptor: a model for the study of chemoattractant receptor structure and function. *Pharmacol. Ther.* 74:73.

Le, Y., J. Hu, W. Gong, W. Shen, B. Li, N. M. Dunlop, D. O. Halverson, D. G. Blair, and J. M. Wang. 2000. Expression of functional formyl peptide receptors by human astrocytoma cell lines. *J. Neuroimmunol.* 111:102.

Ye, R. D., S. L. Cavanagh, O. Quehenberger, E. R. Prossnitz, and C. G. Cochrane. 1992. Isolation of a cDNA that encodes a novel granulocyte N-formyl peptide receptor. *Biochem. Biophys. Res. Commun.* 184:582.

Gronert, K., A. Gewirtz, J. L. Madara, and C. N. Serhan. 1998. Identification of a human enterocyte lipoxin A4 receptor that is regulated by interleukin (IL)-13 and interferon gamma and inhibits tumor necrosis factor alpha-induced IL-8 release. *J. Exp. Med.* 187:1285.

Le, Y., J. J. Oppenheim, and J. M. Wang. 2001. Pleiotropic roles of formyl peptide receptors. *Cytokine Growth Factor Rev.* 12:91.

Le, Y., Y. Yang, Y. Cui, H. Yazawa, W. Gong, C. Qiu, and J. M. Wang. 2002. Receptors for chemotactic formyl peptides as pharmacological targets. *Int. Immunopharmacol.* 2:1.

Yang, D., Q. Chen, A. P. Schmidt, G. M. Anderson, J. M. Wang, J. Wooters, J. J. Oppenheim, and O. Chertov. 2000. LL-37, the neutrophil granule- and epithelial cell-derived cathelicidin, utilizes formyl peptide receptor-like 1 (FPRL 1) as a receptor to chemoattract human peripheral blood neutrophils, monocytes, and T cells. *J. Exp. Med.* 192:1069.

Dahlgren, C., T. Christophe, F. Boulay, P. N. Madianos, M. J. Rabiet, and A. Karlsson. 2000. The synthetic chemoattractant Trp-Lys-Tyr-Met-Val-DMet activates neutrophils preferentially through the lipoxin A(4) receptor. *Blood* 95:1810.

Li, B. Q., M. A. Wetzel, J. A. Mikovits, E. E. Henderson, T. J. Rogers, W. Gong, Y. Le, F. W. Ruscetti, and J. M. Wang. 2001. The synthetic peptide WKYMVm attenuates the function of the chemokine receptors CCR5 and CXCR4 through activation of formyl peptide receptor-like 1. *Blood* 97:2941.

Le, Y., P. M. Murphy, and J. M. Wang. 2002. Formyl-peptide receptors revisited. *Trends Immunol.* 23:541.

Le, Y., W. Gong, H. L. Tiffany, A. Tumanov, S, Nedospasov, W. Shen, N. M. Dunlop, J. L. Gao, P. M. Murphy, J. J. Oppenheim, and J. M. Wang. 2001. Amyloid (beta) 42 activates a G-protein-coupled chemoattractant receptor, FPR-like-1. *J. Neurosci.* 21: RC123.

Le, Y., H. Yazawa, W. Gong, Z. Yu, V. J. Ferrans, P. M. Murphy, and J. M. Wang. 2001. The neurotoxic prion peptide fragment PrP(106-126) is a chemotactic agonist for the G protein-coupled receptor formyl peptide receptor-like 1. *J. Immunol.* 166:1448.

Chiang, N., I. M. Fierro, K. Gronert, and C. N. Serhan. 2000. Activation of lipoxin A(4) receptors by aspirin-triggered lipoxins and select peptides evokes ligand-specific responses in inflammation. *J. Exp. Med.* 191:1197.

Su, S. B., J. Gao, W. Gong, N. M. Dunlop, P. M. Murphy, J. J. Oppenheim, and J. M. Wang. 1999. T21/DP107, A synthetic leucine zipper-like domain of the HIV-1 envelope gp41, attracts and activates human phagocytes by using G-protein-coupled formyl peptide receptors. *J. Immunol.* 162:5924.

Deng, X., H. Ueda, S. B. Su, W. Gong, N. M. Dunlop, J. Gao, P. M. Murphy, and J. M. Wang. 1999. A synthetic peptide derived from human immunodeficiency virus type 1 gp120 downregulates the expression and function of chemokine receptors CCR5 and CXCR4 in monocytes by activating the 7-transmembrane G-protein-coupled receptor FPRL1/LXA4R. *Blood* 94:1165.

Shen, W., P. Proost, B. Li, W. Gong, Y. Le, R. Sargeant, P. M. Murphy, J. Van Damme, and J. M. Wang. 2000. Activation of the chemotactic peptide receptor FPRL1 in monocytes phosphorylates the chemokine receptor CCR5 and attenuates cell responses to selected chemokines. *Biochem. Biophys. Res. Commun.* 272:276.

Back, S. H., J. K. Seo, C. B. Chae, P. G. Suh, and S. H. Ryu. 1996. Identification of the peptides that stimulate the phosphoinositide hydrolysis in lymphocyte cell lines from peptide libraries. *J. Biol. Chem.* 271:8170.

Seo, J. K., S. Y. Choi, Y. Kim, S. H. Back, K. T. Kim, C. B. Chae, J. D. Lambeth, P. G. Suh, and S. H. Ryu. 1997. A peptide with unique receptor specificity: stimulation of phosphoinositide hydrolysis and induction of superoxide generation in human neutrophils. *J. Immunol.* 158:1895.

Le, Y., W. Gong, B. Li, N. M. Dunlop, W. Shen, S. B. Su, R. D. Ye, and J. M. Wang. 1999. Utilization of two seven-transmembrane, G protein-coupled receptors, formyl peptide receptor-like 1 and formyl peptide receptor, by the synthetic hexapeptide WKYMVm for human phagocyte activation. *J. Immunol.* 163:6777.

Libby P. 2002. Inflammation in atherosclerosis. *Nature* 420:868.

He, R., H. Sang, and R. D. Ye. 2003. Serum amyloid A induces IL-8 secretion through a G protein-coupled receptor, FPRL1/LXA4R. *Blood* 101:1572.

Bae, Y. S., H. Bae, Y. Kim, T. G. Lee, P. G. Suh, and S. H. Ryu. 2001. Identification of novel chemoattractant peptides for human leukocytes. *Blood* 97:2854.

Hu, J. Y., Y. Le, W. Gong, N. M. Dunlop, J. L. Gao, P. M. Murphy, and J. M. Wang. 2001. Synthetic peptide MMK-1 is a highly specific chemotactic agonist for leukocyte FPRL1. *J. Leukoc. Biol.* 70:155.

Grynkiewicz, G., M. Poenie, and R. Y. Tsien. 1985. A new generation of Ca2+ indicators with greatly improved fluorescence properties. *J. Biol. Chem.* 260:3440.

Narenjkar, J., S. J. Marsh, and E. S. Assem. 1999. The characterization and quantification of antigen-induced Ca2+ oscillations in a rat basophilic leukaemia cell line (RBL-2H3). *Cell. Calcium.* 26:261.

Yazawa, H., Z. X. Yu, K. Takeda, Y. Le, W. Gong, V. J. Ferrans, J. J. Oppenheim, C. C. Li, and J. M. Wang. 2001. Beta amyloid peptide (Abeta42) is internalized via the G-protein-coupled receptor FPRL1 and forms fibrillar aggregates in macrophages. *FASEB J.* 15, 2454-2462.

Hampton, M. B., A. J. Kettle, and C. C. Winterbourn. 1998. Inside the neutrophil phagosome: oxidants, myeloperoxidase, and bacterial killing. *Blood* 92:3007.

Tiffany, H. L., M. C. Lavigne, Y. H. Cui, J. M. Wang, T. L. Leto, J. L. Gao, and P. M. Murphy. 2001. Amyloid-beta induces chemotaxis and oxidant stress by acting at formylpeptide receptor 2, a G protein-coupled receptor expressed in phagocytes and brain. *J. Biol. Chem.* 276:23645.

Freer, R. J., A. R. Day, J. A. Radding, E. Schiffmann, S. Aswanikumar, H. J. Showell, and E. L. Becker. 1980. Further studies on the structural requirements for synthetic peptide chemoattractants. *Biochemistry* 19:2404.

Dalpiaz, A., R. Pecoraro, G. Vertuani, S. Spisani, O. Rizzuti, E. Fabbri, and A. Scatturin. 1999. Formylpeptide receptor antagonists: structure and activity. *Boll. Chim. Farm.* 138:44.

Wenzel-Seifert, K., L. Grunbaum, and R. Seifert. 1991. Differential inhibition of human neutrophil activation by cyclosporins A, D, and H. Cyclosporin H is a potent and effective inhibitor of formyl peptide-induced superoxide formation. *J. Immunol.* 147:1940.

Wenzel-Seifert, K., and R. Seifert. 1993. Cyclosporin H is a potent and selective formyl peptide receptor antagonist. Comparison with N-t-butoxycarbonyl-L-phenylalanyl-L-leucyl-L-phenylalanyl-L-leucyl-L-phenylalanine and cyclosporins A, B, C, D, and E. *J. Immunol.* 150:4591.

de Paulis, A., A. Ciccarelli, G. de Crescenzo, R. Cirillo, V. Patella, and G. Marone. 1996. Cyclosporin H is a potent and selective competitive antagonist of human basophil activation by N-formyl-methionyl-leucyl-phenylalanine. *J. Allergy Clin. Immunol.* 98:152.

Vagnucci, A. H. Jr, and W. W. Li. 2003. Alzheimer's disease and angiogenesis. *Lancet* 361:605.

Checker, F., and B. Vincent. 2002. Alzheimer's and prion diseases: distinct pathologies, common proteolytic denominators. *Trends. Neurosci.* 25: 616.

Schubert, P., T. Ogata, H. Miyazaki, C. Marchini, S. Ferroni, and K. Rudolphi. 1998. Pathological immuno-reactions of glial cells in Alzheimer's disease and possible sites of interference. *J. Neural. Transm. Suppl.* 54:167.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A polypeptide comprising a W-rich peptide having SEQ ID NO:4.

2. A mimic of the polypeptide according to claim 1, wherein the mimic polypeptide binds to a formyl peptide receptor (FPR) class receptor and inhibits its activity.

3. A pharmaceutical composition comprising the polypeptide according to claim 1.

4. The polypeptide according to claim 1, which is from 6 to 15 amino acids long.

5. The polypeptide according to claim 4, which is from 6 to 10 amino acids long.

6. The polypeptide according to claim 5, which is from 6 to 7 amino acids long.

7. The polypeptide according to claim 6, which is 6 amino acids long.

* * * * *